(12) United States Patent
Bolger et al.

(10) Patent No.: US 7,011,410 B2
(45) Date of Patent: Mar. 14, 2006

(54) METHOD AND APPARATUS FOR MONITORING EYE TREMOR

(75) Inventors: Ciaran Bolger, Dublin (IE); Steven W. Arms, Williston, VT (US); Christopher P. Townsend, Shelburne, VT (US); Kurt R. Smith, Boulder, CO (US)

(73) Assignee: EyeTect, L.L.C., Belleville, IL (US)

( * ) Notice: Subject to any disclaimer, the term of this patent is extended or adjusted under 35 U.S.C. 154(b) by 597 days.

(21) Appl. No.: 09/988,629

(22) Filed: Nov. 20, 2001

(65) Prior Publication Data

US 2002/0085174 A1 Jul. 4, 2002

Related U.S. Application Data

(60) Provisional application No. 60/252,429, filed on Nov. 22, 2000.

(51) Int. Cl.
*A61B 3/14* (2006.01)

(52) U.S. Cl. .................. 351/209; 351/205; 600/558; 606/4

(58) Field of Classification Search ............ 351/209, 351/205, 210, 41; 600/501, 558, 595; 128/898; 606/4, 5, 6
See application file for complete search history.

(56) References Cited

U.S. PATENT DOCUMENTS

| | | | |
|---|---|---|---|
| 4,006,974 A | * | 2/1977 | Resnick .................. 351/41 |
| 4,572,199 A | | 2/1986 | LaCourse |
| 4,836,219 A | | 6/1989 | Hobson et al. |
| 4,852,988 A | * | 8/1989 | Velez et al. ............. 351/210 |
| 4,863,259 A | * | 9/1989 | Schneider et al. ....... 351/210 |
| 5,305,746 A | | 4/1994 | Fendrock |
| 5,320,109 A | | 6/1994 | Chamoun et al. |
| 5,345,281 A | * | 9/1994 | Taboada et al. .......... 351/210 |
| 5,368,041 A | | 11/1994 | Shambroom |
| 5,381,804 A | | 1/1995 | Shambroom |
| 5,410,376 A | * | 4/1995 | Cornsweet et al. ....... 351/210 |
| 5,458,117 A | | 10/1995 | Chamoun et al. |
| 5,792,069 A | | 8/1998 | Greenwald et al. |
| 5,813,404 A | | 9/1998 | Devlin et al. |
| 5,980,513 A | * | 11/1999 | Frey et al. .............. 351/209 |
| 6,032,064 A | | 2/2000 | Devlin et al. |
| 6,032,072 A | | 2/2000 | Greenwald et al. |
| 6,271,915 B1 | | 8/2001 | Frey et al. |
| 6,542,081 B1 | * | 4/2003 | Torch ..................... 600/558 |
| 6,568,808 B1 | * | 5/2003 | Campin ................... 351/209 |
| 6,634,749 B1 | * | 10/2003 | Morrison et al. ......... 351/209 |

OTHER PUBLICATIONS

Davis Coakley; "The Ocular Microtremor Record and the Prognosis of the Unconscious Patient," The Lancet; Mar. 5, 1977; pp. 512–515.

Alexander Spauschus; Jon Marsden; David M. Halliday; Jay R. Rosenberg; Peter Brown; "The Origin of Ocular Microtremor in Man;" Experimental Brain Research; 1999; pp. 556–562.

(Continued)

*Primary Examiner*—Fadi H. Dahbour
(74) *Attorney, Agent, or Firm*—Finnegan, Henderson, Farabow, Garrett & Dunner, L.L.P.

(57) ABSTRACT

An apparatus consistent with the present invention comprises a sensor for receiving a signal representing eye tremor and a processor for monitoring eye tremor while receiving the signal. A method consistent with the present invention includes receiving a signal representing eye tremor, comparing the received signal representing eye tremor to at least one reference value, and classifying a patient's brain stem function using the comparison of the received signal representing eye tremor to at least one reference value. An embodiment consistent with the present invention includes an ocular micro tremor (OMT) sensor and associated signal processing hardware and software for clinical analyses.

6 Claims, 19 Drawing Sheets

OTHER PUBLICATIONS

Veroslav Golda; Rudolf Petr, Frantisek Cermak, Vladimir Rozsival; Aromir Sverak; Ocular Microtremor and the Level of Vigilance; pp. 77–83.

W.L. Davies; G.R. Plant; "A Transducer for the Clinical Recording of Ocular Microtremor;" vol. 2, No. 5; Sep., 1978; pp. 249–251.

Peter Brown, M.D.; "A New Clinical Technique for Demonstrating Changes in Eye Acceleration During Horizontal Saccades in Patients with Partial Internuclear Ophthalmoplegias;" Journal of Neuro–Ophthalmology; vol. 18, No. 1; 1988; pp. 36–39.

W.L. Davies; G.R.: Plant; "The Recording and Analysis of Human Ocular Microtremor;" The Journal of Physiology; Dec., 1977; pp. 21P–22P.

D. Coakley; J.G. Thomas; "The Effect of Age and Eye Position on the Normal Ocular Microtremor Record;" Proceedings of the Physiological Society; Sep., 1976; pp. 260P–261P.

Dr. Davis Coakley; Dr. John D. Thomas; "Ocular Microtremor: A Neurogenic Phenomenon;" Electromyography and Clinical Neurophysiology; 1979; vol. 19, No. 4; pp. 325–328.

S. Bojanic; T. Simpson; C. Bolger; "Ocular Microtremor; A Tool for Measuring Depth of Anaesthesia?;" British Journal of Anaesthesia; 2001; vol. 86, No. 4; pp. 519–522.

Ciaran Bolger; Stana Bojanic; Noirin F. Sheahan; Davis Coakley; James F. Malone; "Effect of Age on Ocular Microtremor Activity;" Journal of Gerontology: Medical Sciences; 2001; vol. 56A, No. 6; pp. M386–M390.

L.Y. Abakumova; A.R. Shakhnovich; J.G. Thomas; An Investigation of the Correlation between Abnormal Patterns of Ocular Microtremor and an Abnormal Pupil Reflex in Neurological Patients; Journal of Neurological Sciences; Dec., 1975; vol. 26, No. 4, pp. 469–477.

M. Michalik; "Spektralanalysen des okularen Mikrotremors bei Hirnstammfunktionsstorunge;" Z. EEG–EMG; No. 18; 1987; pp. 20–26.

"New Clinical and Pathophysiological Aspects of Neuromonitoring," Stana Bojanic and Ciaran Bolger, Program of the First Workshop–Neurosurgery, Neuroanesthesia and Critical Care Medicine, Dec. 11/12$^{th}$; 1998 in Halle/S, Germany.

Ciaran Bolger, Ph.D. et al., "Ocular Microtremor in Brain Stem Death," Neurosurgery, vol. 44 No. 6, pp. 1201–1206, (Jun. 1999).

Ciaran Bolger, Ph.D. et al., "Ocular Microtremor (OMT)" A New Neurophysiological Approach to Multiple Sclerosis, J. Neurol Neurosurg. Psychiatgry, 68:639–642 (2000).

PCT Notification of Transmittal of the International Search Report or the Declaration; PCT International Search Report, Aug. 6, 2002.

H. Bengi and J.G. Thomas, "Three Electronic Methods for Recording Ocular Tremor," Med. & Biol. Engng. vol. 1, pp. 171–179, Pergamon Press (1968).

Davis Coakley, and John G. Thomas, "The Ocular Microtremor Record and the Prognosis of the Unconscious Patient," The Lancet, pp. 512–515, (Mar. 1977).

A.W. Shiri, "Technical Note: Noncontact Method of Measuring the Frequency and Amplitude of the Microtremor of the Eye Through the Closed Eyelid," Med. & Biol. Eng. & Comput., pp. 18, (1980).

Věroslav Golda, Rudolf Petr, František Čermāk, Vladimir Rozsīval, and Jaromīr Svěrák, "Ocular Microtremor and the Level of Vigilance, Department of Neurosurgery and Division of Experimental Neurosurgery," pp. 77–82 (1981).

C. Bolger, N. Sheahan, D. Coakley, and J. Malone, "High Frequency Eye Tremor: Reliability of Measurement," Clin. Phys. Physiol. Meas., vol. 13, No. 2, pp. 151–159, (1992).

N.F. Sheahan, D. Coakley, F. Hegarty, C. Bolgar, and J. Malone, "Ocular Microtremor Measurement System: Design and Performance," Med. & Biol. Eng. & Comput., pp. 205–212, (May 1993).

Ciaran Bolger, Stana Bojanic, Noirin F. Sheahan, Davis Coakley, and James F. Malone, "Ocular Microtremor in Patients with Idiopathic Parkinson's Disease," Jour. of Neuro & Psych., vol. 66, No. 4:528–531 (Apr. 1999).

Ciaran Bolger, Stana Bojanic, Noirin F. Sheahan, Davis Coakley, and James F. Malone, "Dominant Frequency Content of Ocular Mirotremor from Normal Subjects," Vision Research, vol. 39, pp. 1911–1915, (1999).

Ciaran Bolger, Stana Bojanic, Noirin F. Sheahan, Davis Coakley, and James F. Malone, "Ocular Microtremor in Oculomotor Palsy," Jour. of Neuro–Ophth., vol. 19, 1:42–45, (1999).

Ciaran Bolger, Ph.D., "Ocular Microtremor: Reliability of Measurement, Physiological Variation and Neurogenic Origin," Thesis T.C.D., pp. 1–240, (1994).

Davis Coakley, "The Effect of Anaesthesia on Ocular Microtremor," Minute Eye Movement and Brain Stem Function, CRC Press, pp. 49–89.

* cited by examiner

METHOD AND APPARATUS FOR MONITORING EYE TREMOR

This application claims the benefit of Provisional Application Ser. No. 60/252,429, filed Nov. 22, 2000.

BACKGROUND OF THE INVENTION

The present invention relates generally to signal processing systems and methods, and more particularly to systems that monitor eye tremor signals.

This application claims priority to Provisional U.S. Patent Application entitled "Method and Apparatus for Monitoring Eye Tremor," Ser. No. 60/252,429, filed Nov. 22, 2000, and is herein incorporated by reference in its entirety.

Presently the diagnosis of brain stem death is made by judging clinical criteria alone such as pupillary response to light, corneal reflex, absent motor response with painful stimulus to both trigeminal distribution and periphery, gag reflex, cough reflex, oculocephalic reflex, vestibulo ocular reflex and apnoea test. Clinical evidence alone, which is subject to human error, may not be sufficient to establish such an important diagnosis as brain stem death. Research effort in recent years has been directed to the problem of early prognosis in coma. Accurate early prognosis would allow the concentration of expensive, emotionally draining and time consuming therapeutic measures on patients with a real prospect of recovery. Currently accepted methods of measuring depth of coma include the Glasgow Coma Score (GCS), pupillary responsiveness, systolic hypotension, age, intracranial pressure, radiographic findings, and the vestibulo-ocular reflex (VOR). These methods, however, have not had a widespread impact on clinical management of comatose patients, as the likelihood of false prediction is as high as 20%.

A variety of clinical monitors have also been used in order to assess depth of anesthesia and other brain stem activity including, for example, autonomic signs, EEG, isolated forearm technique, auditory evoked responses, oesophageal contractility and surface EMG, but each method has its limitations. At present, the anesthetist's main source of information on the depth of anesthesia is the patient's somatic and autonomic response to surgical stimuli. These responses are modified by neuromuscular blocking drugs and drugs affecting the autonomic nervous system. The presence or absence of these responses does not, however, correlate with conscious awareness and at times they can be inadequate indicators of a satisfactory depth of anesthesia. Therefore, there is a need for a method and apparatus to adequately measure depth of anesthesia and other conditions correlated with eye tremor.

SUMMARY OF THE INVENTION

Methods and apparatus consistent with this invention monitor eye tremor. An apparatus consistent with the present invention comprises a sensor for receiving a signal representing eye tremor and a processor for monitoring eye tremor while receiving the signal. A method consistent with the present invention includes receiving a signal representing eye tremor, comparing the received signal representing eye tremor to at least one reference value, and classifying a patient's brain stem function using the comparison of the received signal representing eye tremor to at least one reference value.

An embodiment consistent with the present invention includes an ocular micro tremor (OMT) sensor and associated signal processing hardware and software for clinical analyses, including, for example, monitoring depth of anesthesia, assessing brain damage, determining a subject's level of consciousness, determining a coma prognosis, determining coma depth, and supporting other applications of brain stem activity monitoring that will be apparent from the subsequent description of embodiments consistent with the invention.

An embodiment of the present invention is a low cost, and potentially disposable, miniature OMT sensor for monitoring eye tremor through the closed eyelid. An embodiment of the present invention uses signal conditioning circuitry in a manner that can reduce artifacts that could result from electromagnetic interference (EMI). An embodiment consistent with the present invention includes a signal processing module which acquires, analyzes, and displays OMT data with minimal input or attendance by clinical personnel.

Both the foregoing general description and the following detailed description are exemplary and explanatory and are intended to provide further explanation of the invention as claimed.

DESCRIPTION OF THE FIGURES

The accompanying drawings provide a further understanding of the invention. They illustrate embodiments of the invention and, together with the description, explain the principles of the invention.

DETAILED DESCRIPTION OF THE INVENTION

Figure 1:
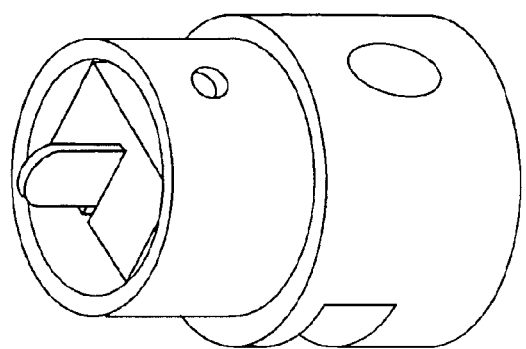
FIG. 1 is an exploded view of an apparatus for monitoring eye tremor consistent with the present invention.
Figure 1:
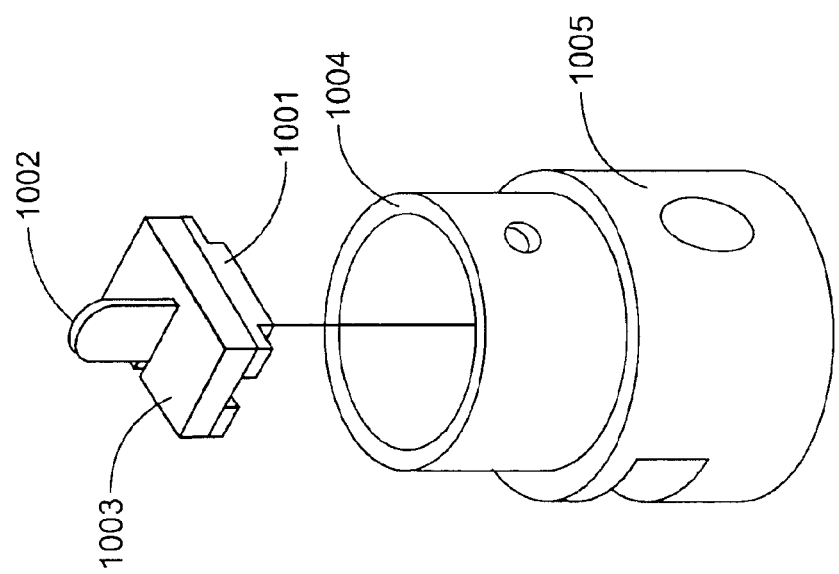

Reference will now be made in detail to preferred embodiments illustrated in the accompanying drawings. The same numbers in different figures refer to like or similar elements.

Ocular microtremor is a fine, high frequency tremor of the eyes which is caused by extraocular muscle activity stimulated by constant impulses emanating in the brain stem. It should be noted that neural activity from other areas, namely the frontal eye fields (also known as areas 6 and 8), the inferior parietal cortex and cerebellum also influence the oculomotor nuclei.

OMT was described as one of the three fixational eye movements in 1934 by F. H. Alder and F. Fliegelman in a paper entitled "The influence of fixation on the visual acuity," Arc. Ophthal., vol. 12, pp. 475–483, (1934). OMT is present in individuals even when the eyes are at rest and has only recently been appreciated as a primarily neurological phenomenon. The frequency of this tremor is reduced in patients whose consciousness is reduced by anesthesia or head injury whereas amplitude falls with anesthesia and sleep but may increase during coma. Therefore, OMT frequency and/or amplitude can be an indication of an individual s level of awareness or consciousness.

Observing OMT is useful in assessing the status of patients in various conditions. Applications of an eye tremor monitoring system consistent with the present invention include, but are not limited to, the following:

monitoring patients with motor neuron disease studying the effect of age on ocular microtremor activity monitoring ocular microtremor activity in comatose subjects to determine coma prognosis measuring the dominant frequency content of ocular microtremor from normal subjects using ocular microtremor to assess the status of patients with multiple sclerosis using ocular microtremor to assess the status of patients with oculomotor palsy using ocular microtremor to assess the status of patients with idiopathic Parkinson's disease monitoring the status of patients under anesthesia to determine, for example, depth of anesthesia during surgery measuring the frequency spectra for ocular microtremor classifying a subject's meditative state conducting sleep pattern analysis measuring combat readiness diagnosing brain stem death monitoring general brain stem function An embodiment of an eye tremor monitoring system consistent with the present invention compares a signal representing eye tremor of a patient to at least one reference value representing, for example, a normal eye tremor. The normal eye tremor record consists of an irregular baseline tremor superimposed on what are regular sinusoidal bursts of activity. An embodiment of the present invention monitors OMT in real-time. Although some embodiments of an eye tremor monitoring system consistent with the present invention compare a subject's eye tremor signal to a reference value representing normal eye tremor, there is no universally preferred normal eye tremor reference value. Instead, reference values representing normal eye tremor can vary among subjects. For example, in normal, healthy subjects, OMT frequency ranges from 50–100 Hz. The mean frequency of OMT in normal healthy subjects is approximately 84 Hz with a standard deviation +/−6 Hz. Studies to-date have not found significant differences in normal OMT frequency attributable to the sex of a subject. One study of subjects above 70 years of age, however, found that the mean peak count frequency of the subjects was around 80 Hz (see "Dominant Frequency Content of Ocular Microtremor from Normal Subjects," C. Bolger, S. Bojanic, N. Sheahan, D. Coakley, and J. Malone. Vision Research, vol. 39, pp. 1911–1915 (1999). Researchers have since suggested that different values of "normal" should apply to individuals above 60 years of age.

Accordingly, because the OMT frequency indicating a "normal" state can vary from subject to subject, embodiments consistent with the present invention have the flexibility to compare a subject's eye tremor signal with a reference value that is appropriate for the subject being monitored. One example of an appropriate reference value would be a function such as taking a percentage of a baseline reading for the subject. Another example of an appropriate reference value, which would be suitable if a baseline was not available, is a reference value representing an average normal value for a representative population of subjects.

By comparing normal values of OMT frequency to patient OMT when embodiments consistent with the present invention are used, for example, in an operating room, one can more objectively determine the patient's level of consciousness for proper administration of anesthetics, which reduces the risk of over or under dosage. Comparing normal OMT frequency values to those of subjects in a comatose state can assist in determining the patient's prognosis. And, OMT readings can provide a more objective diagnosis of brain stem death, which can save substantial critical care costs as well as optimize organ donation opportunities.

The mean OMT peak count frequency in a subject being anesthetized can drop progressively at predicted plasma propofol levels of 1 mcg.ml-1 and 2 mcg.ml-1 and then can plateau out between 3 mcg.ml-1 and 5 mcg.ml-1. Moreover, subjects can lose consciousness at predicted plasma concentrations of 3 mcg.ml-1. At these levels of anesthesia, subjects can have a peak count frequency above 55 Hz. After loss of consciousness, OMT activity can remain below 55 Hz. In some situations, there is no significant difference between mean peak count frequency at loss of consciousness and readings taken thereafter, even at increasing predicted plasma propofol levels. There can be a significant difference between the last awake OMT recording and the first recording taken at loss of consciousness (for example with probability of <0.001) The actual frequency at which subjects can lose consciousness, however, is variable-ranging from 27 to 55 Hz. An alternative predictor of the actual mean peak count frequency at which there will be a loss of consciousness in each subject would be to calculate a percentage of the baseline frequency for each subject. Setting, for example, a value of 45% of the baseline frequency for each subject would be an appropriate OMT frequency threshold for monitoring loss of consciousness. Accordingly, OMT activity can vary with awareness. With regards to depth of anesthesia, an increase in OMT above the mean peak count frequency noted at loss of consciousness indicates lightening of anesthetic depth.

In addition to OMT frequency, the OMT amplitude is also reduced in subjects whose consciousness is reduced by anesthesia but may increase during coma. Therefore, OMT amplitudes can be an indication of an individual's level of awareness or consciousness. The following are examples of the types of patient monitoring that can be accomplished in accordance with the present invention using OMT amplitude and/or frequency measurements:

OMT amplitude data can indicate an individual's level of awareness or consciousness. As anesthetics are administered to or withdrawn from a patient, the OMT amplitude changes such that lower amplitude correlates with deeper anesthesia and higher amplitude correlates with lighter anesthesia. OMT amplitude behavior usually declines and/or rises at a different rate than OMT frequencies.

OMT amplitude data in combination with OMT frequency data is an indication of an individual's level of awareness or consciousness. In comatose patients, OMT frequency is reduced while OMT amplitude remains at normal levels. It is known that comatose patients also experience sleep cycles during which time both OMT frequency and amplitude decline in the same manner usually exhibited during sleep. It follows that while monitoring a comatose patient, if OMT frequency declines while amplitude remains the same, it is an indication that the clinical status of the patient has declined (i.e., deeper comatose state) as opposed to the patient having entered into a sleep cycle whereby both the frequency and amplitude would have declined.

OMT amplitude data in combination with OMT frequency data indicates when an anesthetized patient has crossed over from consciousness to unconsciousness. If OMT amplitude and frequency levels are at a given fraction of normal tremor, the patient has crossed over from consciousness to unconsciousness.

OMT amplitude data in combination with OMT frequency data indicates when an unconscious anesthetized patient is lightening. If during the course of a surgical procedure the anesthetized patient's OMT frequency increases above the point at which they lost consciousness while the patient's amplitude remains below the point at which they lost consciousness, the patient could be at risk of experiencing awareness while still paralyzed.

OMT amplitude data in combination with OMT frequency data indicates when an anesthetized patient has crossed over from unconsciousness to consciousness. If OMT amplitude and frequencies have risen to the levels at which the patient lost consciousness, it is an indication that the patient has crossed over from unconsciousness to consciousness.

The relationship or behavior between frequency and amplitude (i.e., one changing more dramatically, or how one changes with respect to the other) can indicate, or forecast a certain clinical state or response of the subject. For example, as a patient begins going under anesthesia, the OMT frequency drops rapidly first while the amplitude declines more gradually. On the other end of the procedure the reverse occurs as the patient comes out of anesthesia. That is, the OMT amplitude increases dramatically just following cessation of anesthetic agents and levels off at baseline amplitude before the patient awakens while the frequencies gradually increase to pre-anesthetic levels tracking with the anesthesiologist's subjective awareness scale of 1–10.

Therefore, in addition to the usefulness of OMT frequencies, amplitude can be a reliable "depth" indicator either alone or by using frequency recordings to supplement amplitude information and vice versa. For example, sufficient anesthetic depth may be reached before the amplitude drops as described above, thus holding amplitudes steady and observing frequency behavior is a legitimate approach to managing anesthesia. Or, another application is to have the system warn the anesthesiologist of patient lightening if, during a surgical procedure, the amplitude increases but the frequency does not.

OMT is an accurate and objective indicator of depth of coma. Not only is OMT in comatose patients abnormal, but it is also significantly different from normal subjects. OMT frequency is reduced in comatose subjects and the reduction in frequency is related to the depth of coma. Further, there is a correlation between the GCS and OMT frequency as well as an association between abnormality of Vestibulo-Ocular Reflex (VOR) and OMT frequency—GCS and VOR being two of the more widely used and accepted measures of depth of coma currently available. OMT also bears a direct relationship to a comatose patient's prognosis for regaining consciousness. Higher OMT frequencies can indicate a more favorable prognosis while lower frequencies indicate an unfavorable prognosis for regaining consciousness.

Some comatose patients have sleep cycles similar to those in normal subjects (Bricolo et al. 1968; Plum and Posner 1972). The OMT record during sleep differs from that seen during coma in that the former experiences a fall in OMT amplitude while in coma the amplitude may be normal or increased. Accordingly, an eye tremor monitoring apparatus consistent with the present invention can also be used to distinguish between normal sleep state and coma. Moreover, an embodiment of an OMT system consistent with the present invention overcomes limitations in conventional OMT systems by having the ability to record the OMT signal, compute the frequency, and display the results onto a monitor in the operating room (OR) or at bedside on a realtime basis with or without input or attendance by clinical personnel.

An embodiment of an OMT system consistent with the present invention is shown in FIG. 1. The OMT system comprised of a surface mount amplifier 1001, piezoelectric transducer (PZT) 1002, which in this embodiment is comprised of barium titanate ceramic, thin beam, and is constructed and mounted to be sensitive to bending through its thickness, printed circuit board (PCB) 1003, polymer housing 1005, and silicone rubber "brim" 1004. The printed circuit board has a slot designed to receive the thin PZT beam A002 directly, which can provide an alternative to delicate interconnecting leads from the bender to the PC board.

Piezoelectric ceramics are low cost and produce a large response for relatively small mechanical inputs. Piezoelectric polymers may also be employed in the construction of PZT 1002. Alternative sensors consistent with the present invention include, for example, piezoresistive strain gauges, or fiber optic strain gauges, which could be deployed to sense the bending strain in the thin beam. Sensors for recording ocular microtremor signals consistent with the present invention could include, for example, piezoelectric film or transducers, unidirectional microphones or amplifiers, accelerometers, gyroscopes, ultrasound, high resolution micro differential variable reluctance transducers (DVRT), force transducers, pressure sensors and/or velocity sensors, or other microsensors.

Accelerometers are another type of sensor suitable for tremor monitoring. In an embodiment consistent with the present invention, a first accelerometer is mounted on a subject's eyelid and a second accelerometer is mounted on the subject's forehead. The difference in the signal received by the first and second accelerometer is the eye tremor signal of interest. Using two accelerometers tends to assist in reducing the effect of local seismic events (such as minute vibrations in the room) that could distort an eye tremor signal reading. In addition, many types of tremor sensors may be combined with an accelerometer when additional artifacts are being measured (such as cardio-ballistic signals when assessing brain stem death). The difference between the measurements at the sensors can be used to indicate OMT.

In the OMT monitoring device shown in FIG. 1, PZT beam 1002 has metallized electrodes on opposite sides of the beam, which facilitate quick, low cost interconnection to PCB 1003. In an embodiment consistent with the present invention, to prevent direct electrical contact of these electrodes to the surface of the eyelid, PZT beam 1002 is insulated with a thin layer of polyimide. The PCB, PZT, and signal transmitter are insulated by potting and/or coating the PCB assembly within the housing using vacuum pumped medical grade silicone rubber.

Figure 2:
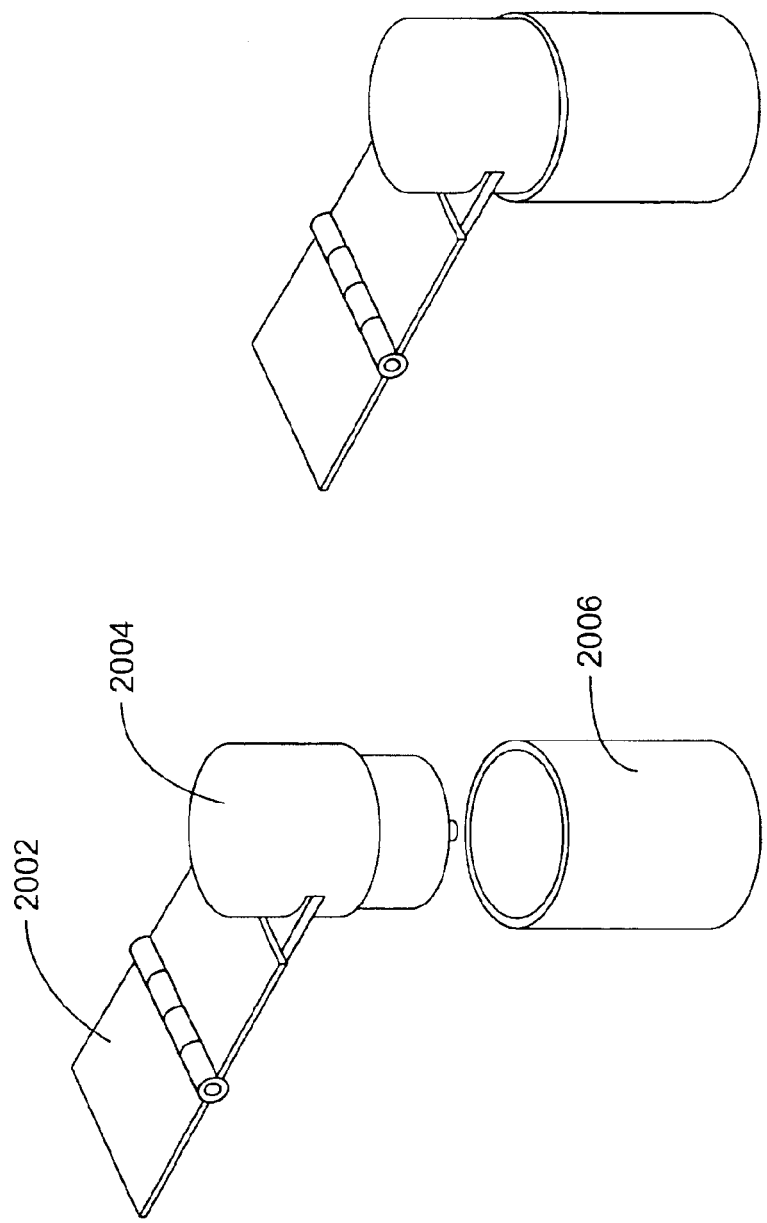
FIG. 2 is a hinged apparatus for monitoring eye tremor consistent with the present invention.

A hinged OMT monitoring device consistent with the present invention as shown in FIG. 2 includes hinged support 2002, polled sensor 2004, and protective sheath 2006.

The hinged OMT monitoring apparatus in FIG. 2 is suitably mounted, using, for example, tape, to the forehead. The housing is lowered to the point where the cornea meets the sclera of the closed eyelid or onto any other suitable area of the eyelid. The housing may also be otherwise adhered in place if more downward pressure is required, such that the sensitive axis of the beam is parallel to the medial-lateral plane of the eye. Silicone rubber brim 1004 provides a comfortable interface to the surface of the eyelid. Movement of the human eye under the closed eyelid, such as OMT, causes mechanical oscillatory input to be applied to PZT 1002, resulting in an output from the PZT which reflects both the frequency of eye movement and the amplitude of the arc of motion of the eye in the medial-lateral plane.

Figure 3:
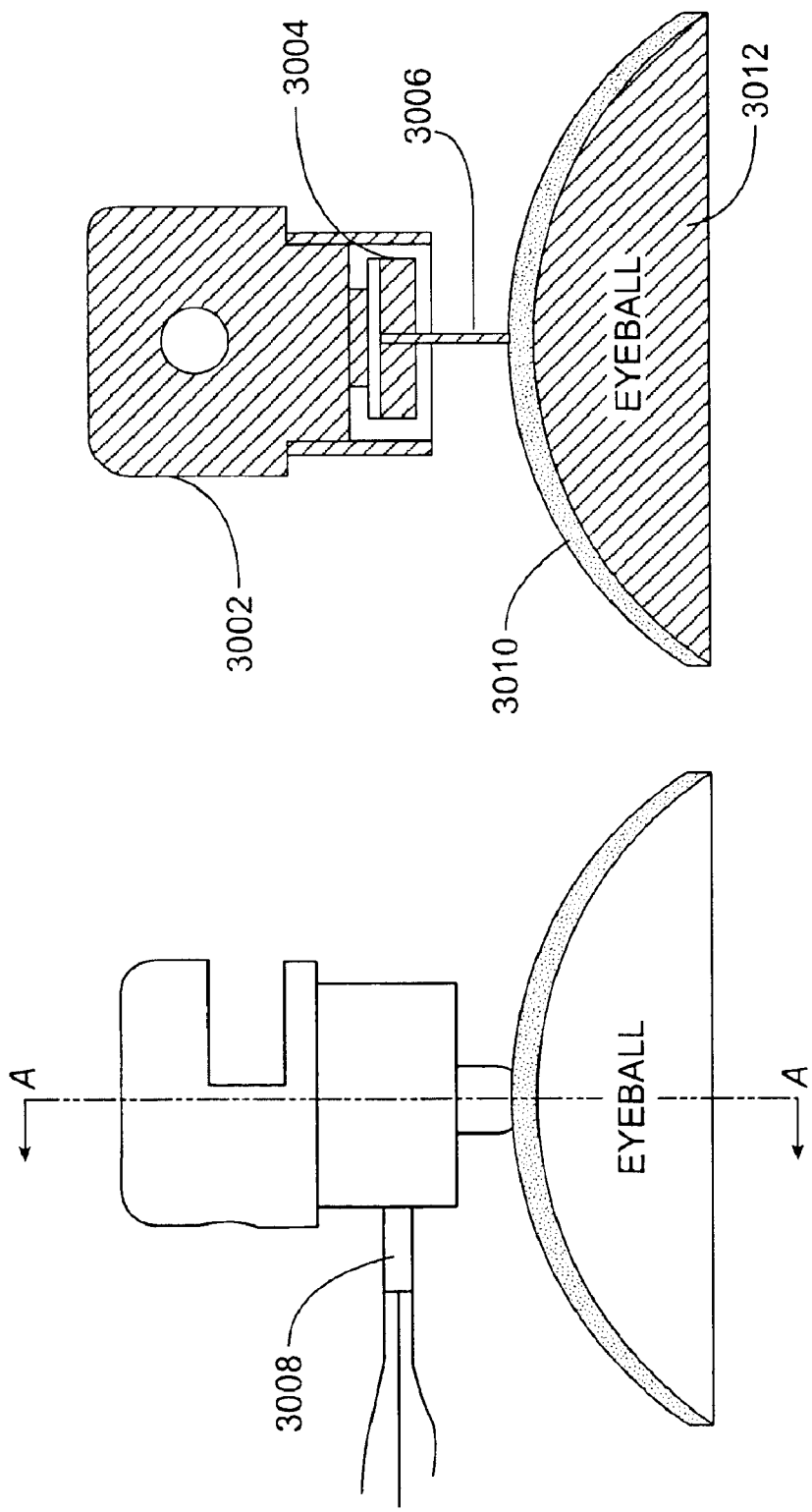
FIG. 3 is a potted eye tremor monitoring apparatus consistent with the present invention.
Figure 4:
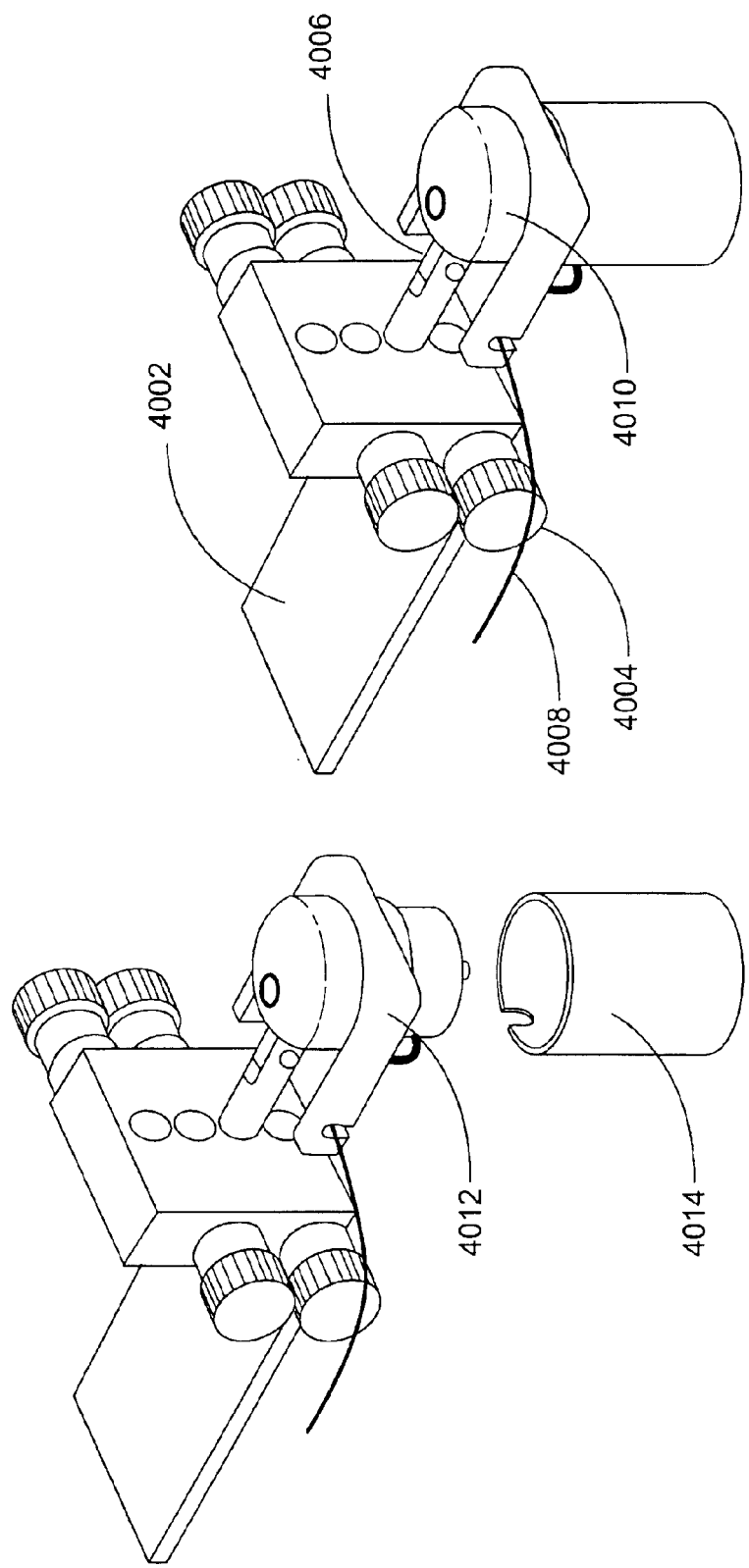
FIG. 4 is a hinged apparatus for monitoring eye tremor consistent with the present invention.
Figure 5:
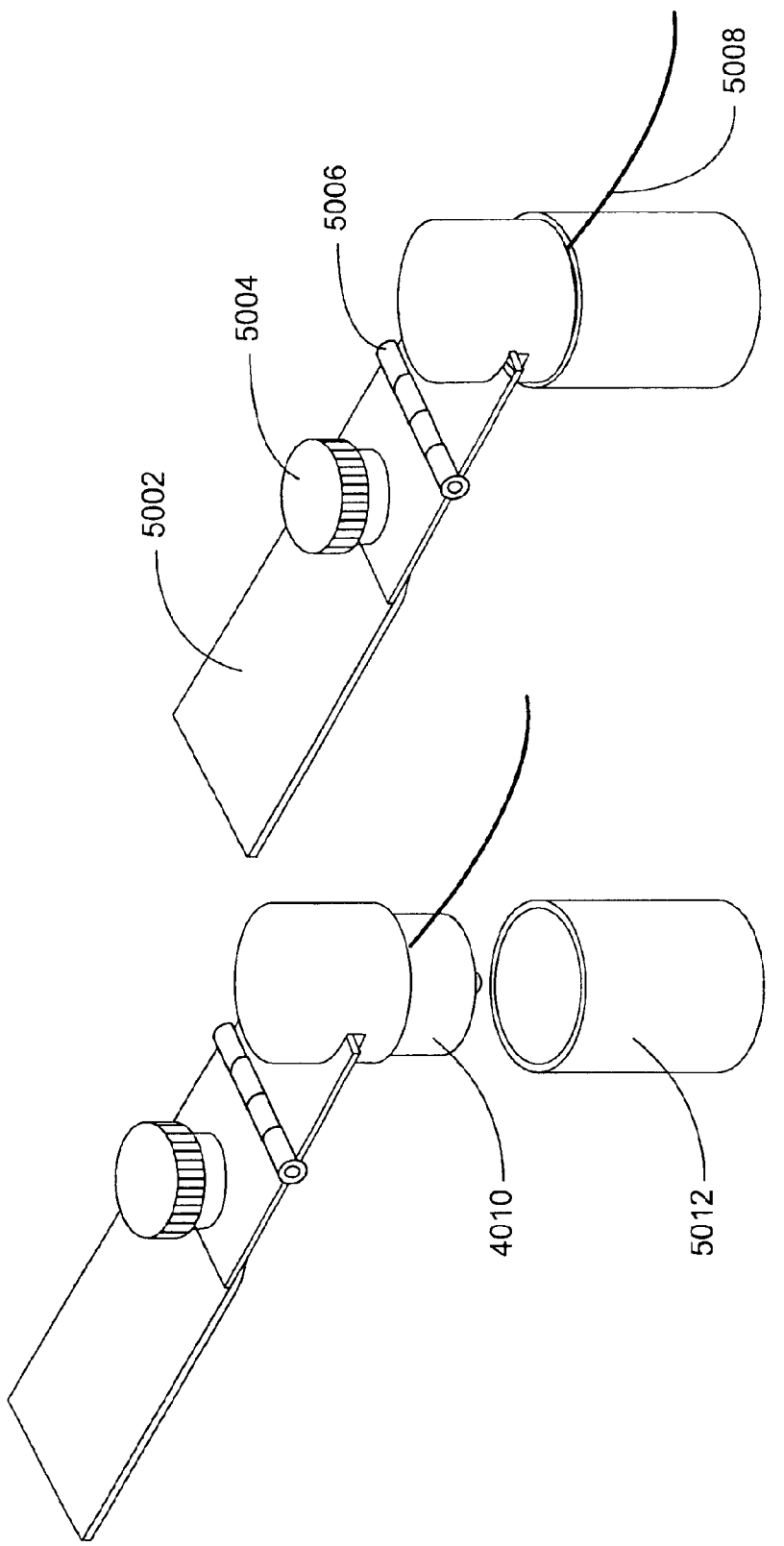
FIG. 5 is a hinged apparatus for monitoring eye tremor consistent with the present invention.

FIG. 3 shows two views of an embodiment of a potted eye tremor monitoring device consistent with the present invention that includes delrin head 3002, printed circuit board (with an optional amplifier) 3004, PZT beam 3006, and cable 3008. PZT beam 3006 contacts eyelid 3010 covering eyeball 3012. FIG. D shows two views of another embodiment of a hinged OMT monitoring device consistent with the present invention including support base 4002, thumb screws 4004, hinged support arm 4006, sensor leads 4008, potted sensor assembly 4010, weight 4012, and protective sheath 4014. FIG. 5 is another embodiment of a hinged OMT monitoring device consistent with the present invention including a hinge extension 5002, thumb screw 5004, hinge 5006, sensor lead 5008, potted sensor assembly and weight 5010, and protective sheath 5012.

In an embodiment consistent with the present invention, the tape used to secure the device to the subject's forehead could also include electrodes that could be used to provide EEG monitoring in addition to its eye tremor monitoring capability. Examples of EEG-based monitoring include conventional EEG monitoring, processed EEG indexes, and auditory evoked responses found within the EEG signal. Such an embodiment provides additional methods for monitoring the subject's brain function so that information can be combined for analysis, or if one system is not functioning properly, another method serves as a check. As an alternative to embedding EEG electrodes in the tape, the electrodes can be embedded in the components supporting the hinge that sits on the subject's forehead. Moreover, one skilled in the art will recognize that there are may possible ways of combining OMT monitoring apparatus with other apparatus for consciousness monitoring in addition to EEG such as auditory evoked potential analysis tools.

PCB 1003 also provides a stable platform for PZT 1002, which, when combined, form a sensing element. A machined area in housing 1005 accepts the PCB by a snap lock interference fit, or, alternatively PCB 1003 may be glued to the housing with epoxy adhesives or the like. An aperture in the housing allows a lead wire to exit from the PCB for connection to signal processing circuitry. Besides providing a platform and interconnect for the bending element, the PCB also provides for direct surface mounting of appropriate filtering devices, such as high pass filtering and signal amplification circuitry. The signal filtering and amplification circuitry can be placed close to the piezoelectric bending element to preserve signal integrity, which, either alone or in combination with filtering software, avoids measuring "noise."

Figure 6:
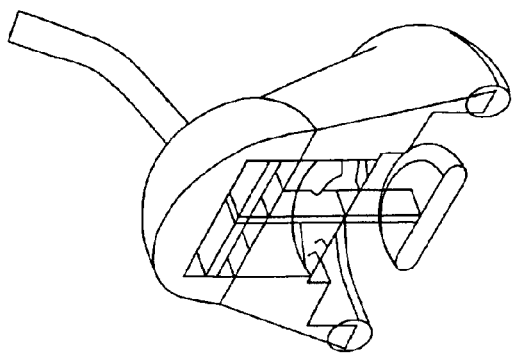
FIG. 6 is an apparatus for monitoring eye tremor with flexure elements consistent with the present invention.
Figure 6:
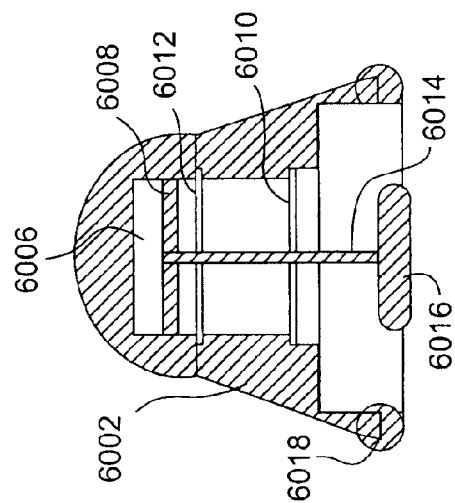
Figure 6:
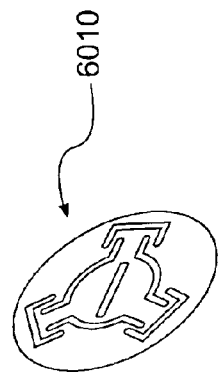
Figure 6:
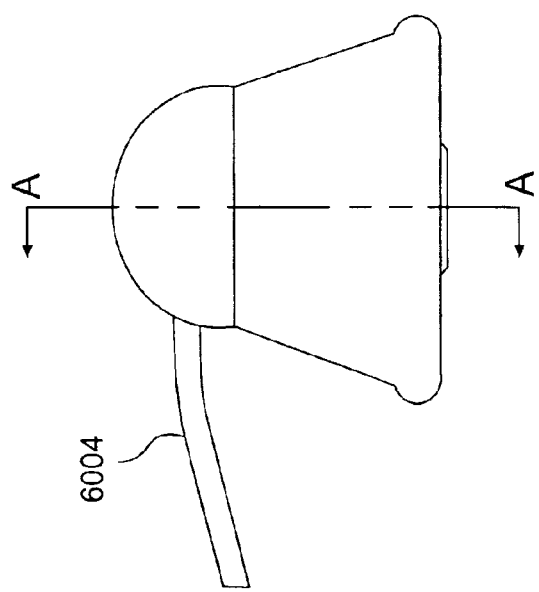
Figure 6:
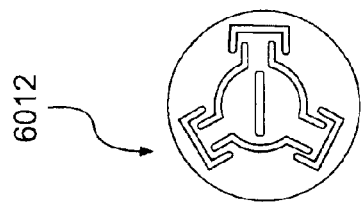

In another embodiment consistent with the present invention, as shown in FIG. 6, a cup-mounted sensor can be used with or without a hinge mount apparatus, for example, as described in greater detail above. The cup-mounted sensor in FIG. 6 comprises a cup 6002, a cable 6004, a cavity 6006, a printed circuit board 6008, flexure 1 6010, flexure 2 6012, a piezo sensor beam 6014, a tip 6016, and an edge 6018.

Cup 6002 can be secured in place over a subject's closed eye lid using tape so that the tip, which is connected to piezo sensor beam 6014, presses onto the portion of the subject's eyelid where the cornea meets the sclera or onto any other suitable location on the subject's eyelid. The bottom rim of cup 6002 forms edge 6018 supporting the sensor apparatus. The edge can be constructed of a soft, rubbery material to prevent the cup from slipping and to cushion the force of the cup on the eyelid. Similarly, tip 6016 attached to piezo sensor beam 6014 is coated with a soft material, such as, for example, silicone rubber to avoid injury.

Piezo sensor beam 6014 is attached to PC board 6008, which is located within the cavity of the cup. Flexures 1 6010 and 2 6012, also inside the cavity, support piezo sensor beam 6014. The flexures exert a force on the piezo sensor beam urging it downward, thereby keeping the tip in contact with the subject's eyelid. The force is controlled by design of the flex in the flexure elements. The force applied must avoid injury. The flexures can be made of, for example, hardened stainless steel or beryllium copper having a thickness in the range of 0.003 to 0.010 inches.

There are many possible embodiments of a tip consistent with the present invention. Tip 6016 is designed to form a contact surface to avoid damage to the subject's eye. In an embodiment consistent with the present invention, the contact surface is a plastic disk. The disk connects to the end of the piezo sensor beam and distributes the force transferred to the sensor along the surface of the disk. Another embodiment of the contact surface consistent with the present invention is a ring that surrounds the cornea, which distributes the sensor force along the ring while avoiding the application of direct pressure to the subject's cornea.

Cable 6004 extending from the cup connects to monitoring equipment that receives the signal generated by piezo sensor beam 6014.

Figure 7:
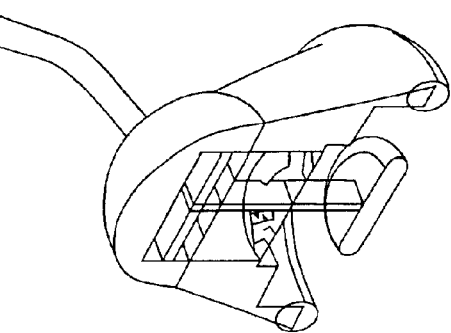
FIG. 7 is an apparatus for monitoring eye tremor with gauged flexure elements consistent with the present invention.
Figure 7:
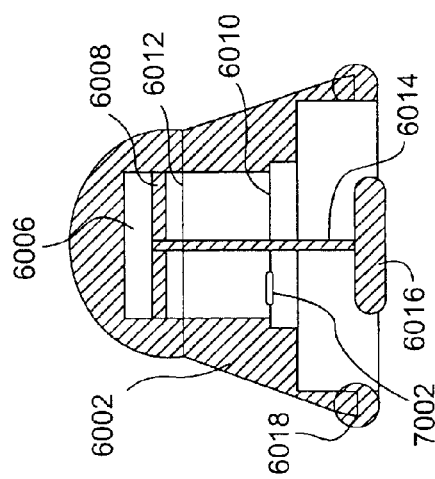
Figure 7:
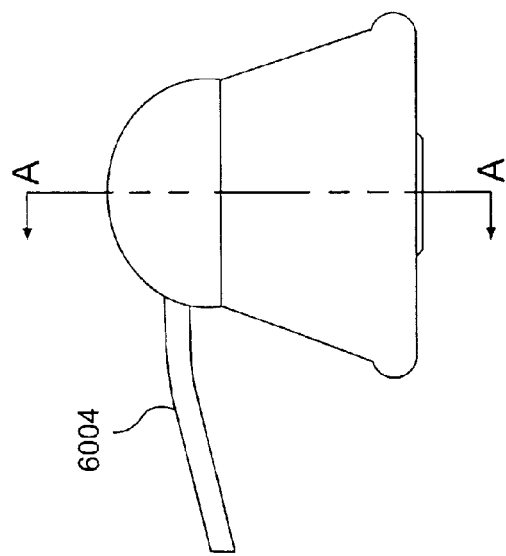
Figure 7:
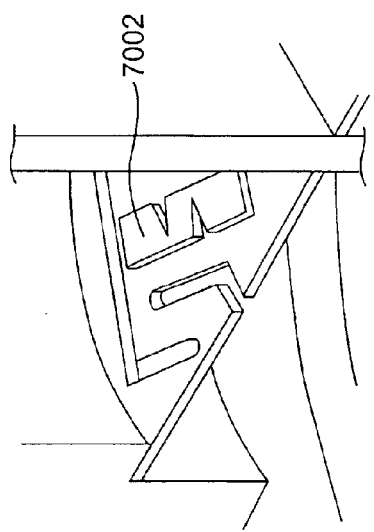

FIG. 7 is a schematic diagram of a cup-mounted sensor consistent with the present invention that includes strain gauge 7002 mounted on flexure 1 7010. A strain gauge can be mounted on either flexure element 1 or 2, or on both flexure elements. A strain gauge mounted on a flexure can provide a signal proportional to the load the piezo sensor beam tip delivers to the closed eyelid. This signal could indicate to an operator whether the tape, or other sensor mounting structure, is providing adequate tension.

Moreover, in an embodiment consistent with the present invention, strain gauges sense lateral movement of the eye and detect eye tremor. The eye tremor signal can be represented as an AC signal superimposed on a DC signal, wherein the DC signal represents bending of the flexures caused by downward pressure against the eyelid. The AC signal represents modulation caused by the subject's eye movement, including OMT.

Figure 8:
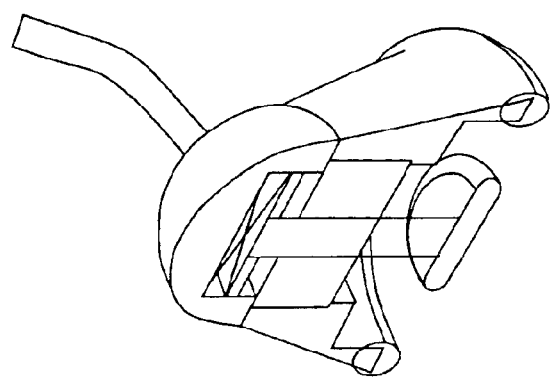
FIG. 8 is an apparatus for monitoring eye tremor with a compression spring and bushing consistent with the present invention.
Figure 8:
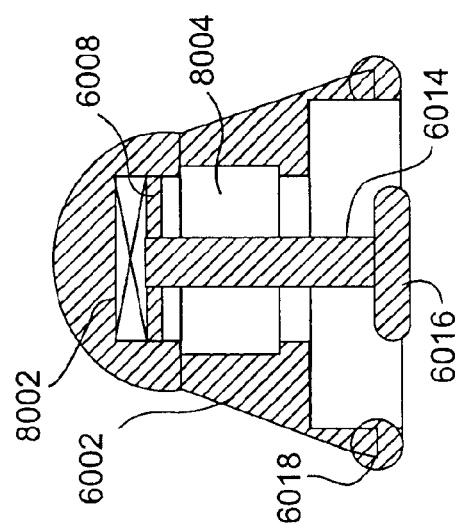
Figure 8:
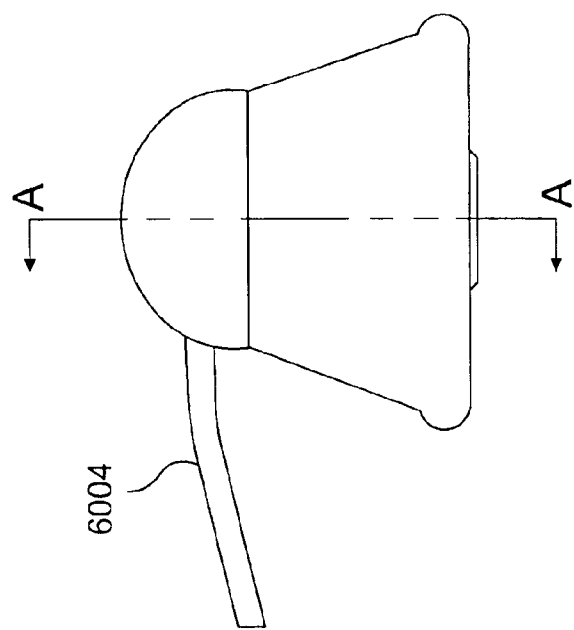

FIG. 8 is a schematic of an embodiment of a system consistent with the present invention similar to the cup-mounted system described above, except that flexures 1 and 2 within the cavity are replaced by compression spring 8002 and bushing 8004. Compression spring 8002 is interposed between cup 6002 and PCB 6008, and delivers a controlled load to the point where the tip contacts the subject's eyelid. The magnitude of the load is controlled by the spring constant of the compression spring and the compression spring displacement. The compression spring displacement is the distance the compression spring extends from the base (lower plane) of the rim of the cup. Both the spring constant and displacement are selected to avoid injuring the patient. Bushing 8004 guides the compression spring to maintain the proper piston action of the piezo sensor beam 6014 and tip 6016.

Figure 9:
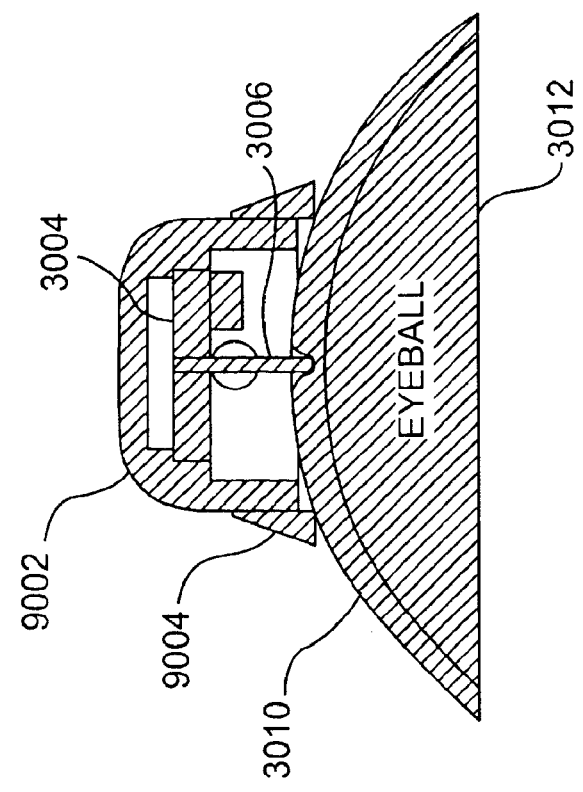
FIG. 9 is a potted eye tremor monitoring apparatus consistent with the present invention.
Figure 9:
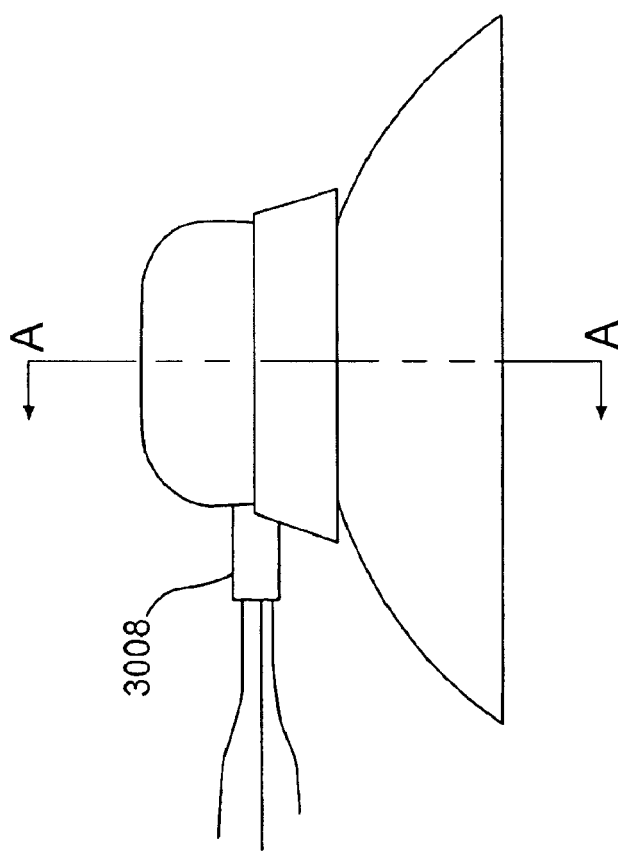
Figure 10:
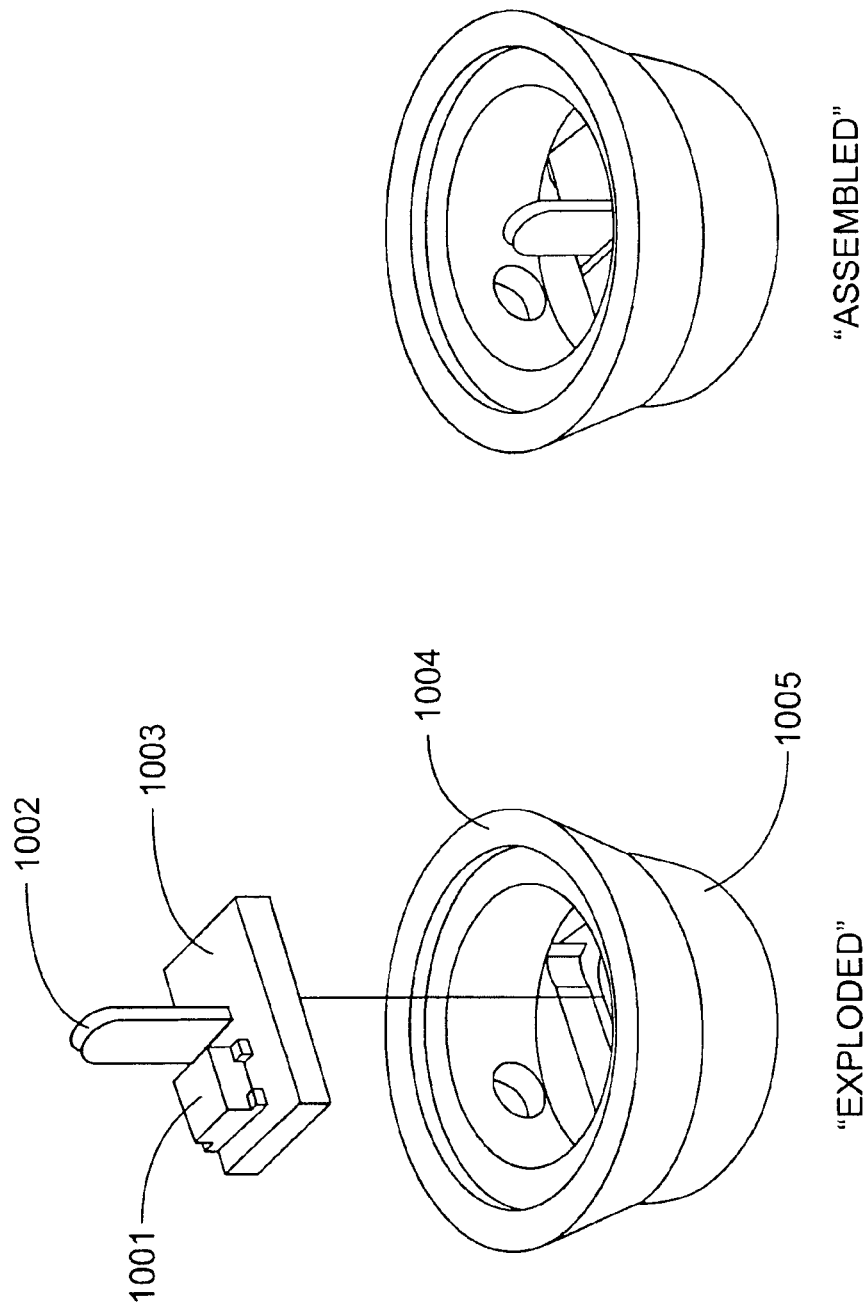
FIG. 10 is a monitoring apparatus consistent with the present apparatus.

FIGS. 9 and 10 are schematics of a system consistent with the present invention as described above with a low profile design. In addition to elements previously described, the embodiment of FIG. 9 includes nylon shell 9002 and silicone flange 9004. The embodiment of FIG. 10 includes elements previously described. The embodiments depicted are suited for low cost production. Tape can be used to secure these low-profile sensors to a subject's eyelid, such that the piezo sensor beam tip contacts the eyelid where the cornea meets the sclera or onto any other suitable location on the subject's eyelid.

When the eye tremor signal received by the sensor drops below a predefined threshold (e.g., 100 millivolts peak-to-peak), a warning message—"LOW OMT SIGNAL"—is displayed on a two line by twenty character display. Possible causes of a low OMT signal include the sensor not being in firm contact with the subject's eyelid, a misplacement of the sensor or absence of brain stem activity. When the sensor is not properly coupled to the subject, an inaccurate measurement can occur; accordingly, the purpose of the warning message is to avoid taking measurements under this condition.

Figure 11:
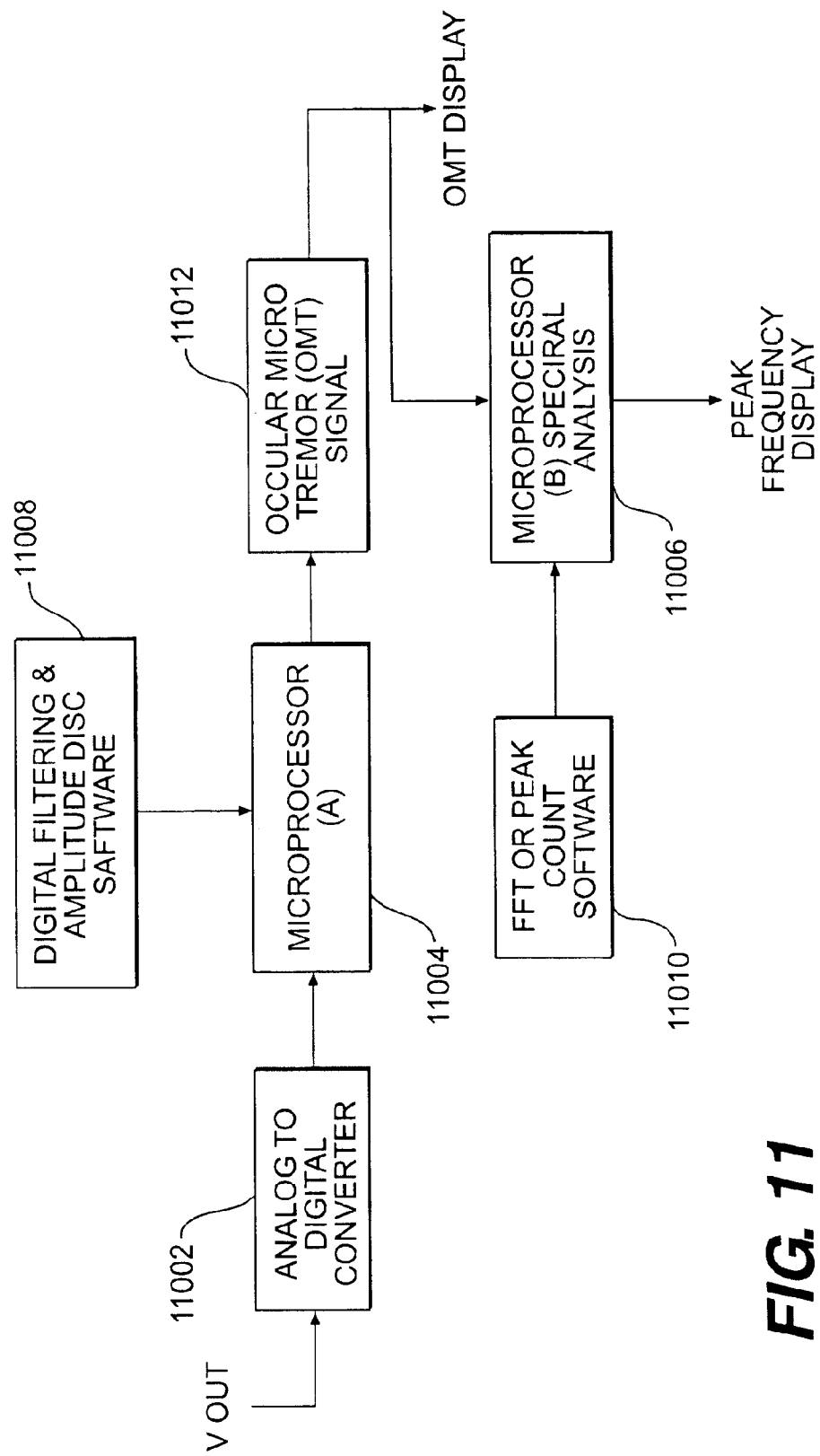
FIG. 11 is a block diagram of an eye tremor monitoring device consistent with the present invention.

Signal-processing techniques are used to interpret the data produced by an OMT system consistent with the present invention. One such signal processing technique consistent with an embodiment of the present invention involves acquiring the OMT signal, rejecting OMT data that may include an artifact (such as a microsaccade), analyzing signal frequency and amplitude, and displaying the result. These steps may be accomplished using, for example, an analog to digital converter 11002, microprocessors 11004 and 11006 (which could also be replaced by a single microprocessor), related software 11008 and 11010, and an LED or LCD display 11012. The A/D converter is used to digitize the analog voltage generated by the OMT sensor and its associated analog filter/amplifier circuitry (FIG. 11).

The microprocessor contains software capable of performing digital filtering, and amplitude discrimination of the incoming OMT signal. This software can recognize input waveforms from the OMT sensor that are relatively large in amplitude, and reject these according to a programmed set of criteria. For example, the software is programmed to filter signals having an amplitude above a preset threshold (e.g., 4.0 volts peak-to-peak). Thus, signals falling above this threshold are not analyzed for OMT content, and a warning message—"HIGH OMT SIGNAL"—is presented on the display.

Large amplitude signals from an eye-mounted sensor can reflect eye activity such as gross eye movements or microsaccades, and these activities tend to mask the desired, true OMT signals. An embodiment of a signal processor consistent with the present invention also has an adaptive filter. This filter is self adjusting and can filter out unwanted signals received by the OMT sensor. An embodiment of the present invention includes a signal processor that changes filter parameters based on signals collected from a subject. For example, the signal processor can sample the OMT signal, compute the average magnitude of the signal, and adjust a threshold to reject signals that are a multiple of the average (e.g., reject signals that have a magnitude that are three times the average).

The microprocessor may also contain software capable of tracking the correlation between OMT frequency and amplitude such that if either one changes while the other holds steady, or changes at a significantly slower or faster rate the system provides an auditory warning and displays a visual message for the operator. For example, if, while a patient is anesthetized, the amplitude increases while the frequency holds steady, the system could audibly beep and display the message "Lightening".

An embodiment of an OMT processor consistent with the present invention is comprised of a processor that executes stored computer program code designed to implement signal processing operations. One skilled in the art will recognize that an embodiment of the signal processor implemented entirely in software, entirely in hardware, or in an embodiment allocating signal processing functions among hardware and software elements, either distributed or centralized, is consistent with the scope of the present invention.

A discriminator parses the data to select an appropriate signal window for spectral analysis (for example, using an FFT and/or peak count algorithm), which is used to measure the highest peak OMT frequency, which is typically in the range of 70–100 Hz for a normal, awake individual. This peak frequency along with the signal window's peak-to-peak amplitude is then sent via a pulse code modulated serial (RS-232) or other digital serial peripheral interface (SPI) output to display driver circuitry, and in turn, to a display of the measured OMT frequency and amplitude. If desired, the corresponding sampled, filtered, and discriminated OMT signal waveform can also be displayed in real-time.

An embodiment of an OMT system consistent with the present invention can transmit the OMT signal waveform to, for example a bedside monitor, printer, intensive care unit monitoring equipment, and any other type of monitoring unit, display unit, or information system either directly attached or, e.g., remotely accessible via a wireless data link. In an embodiment consistent with the present invention, the OMT system generates a signal that can be used to control the medication dosage for the patient being monitored, e.g., the system generates a signal for controlling an infusion pump.

Figure 12:
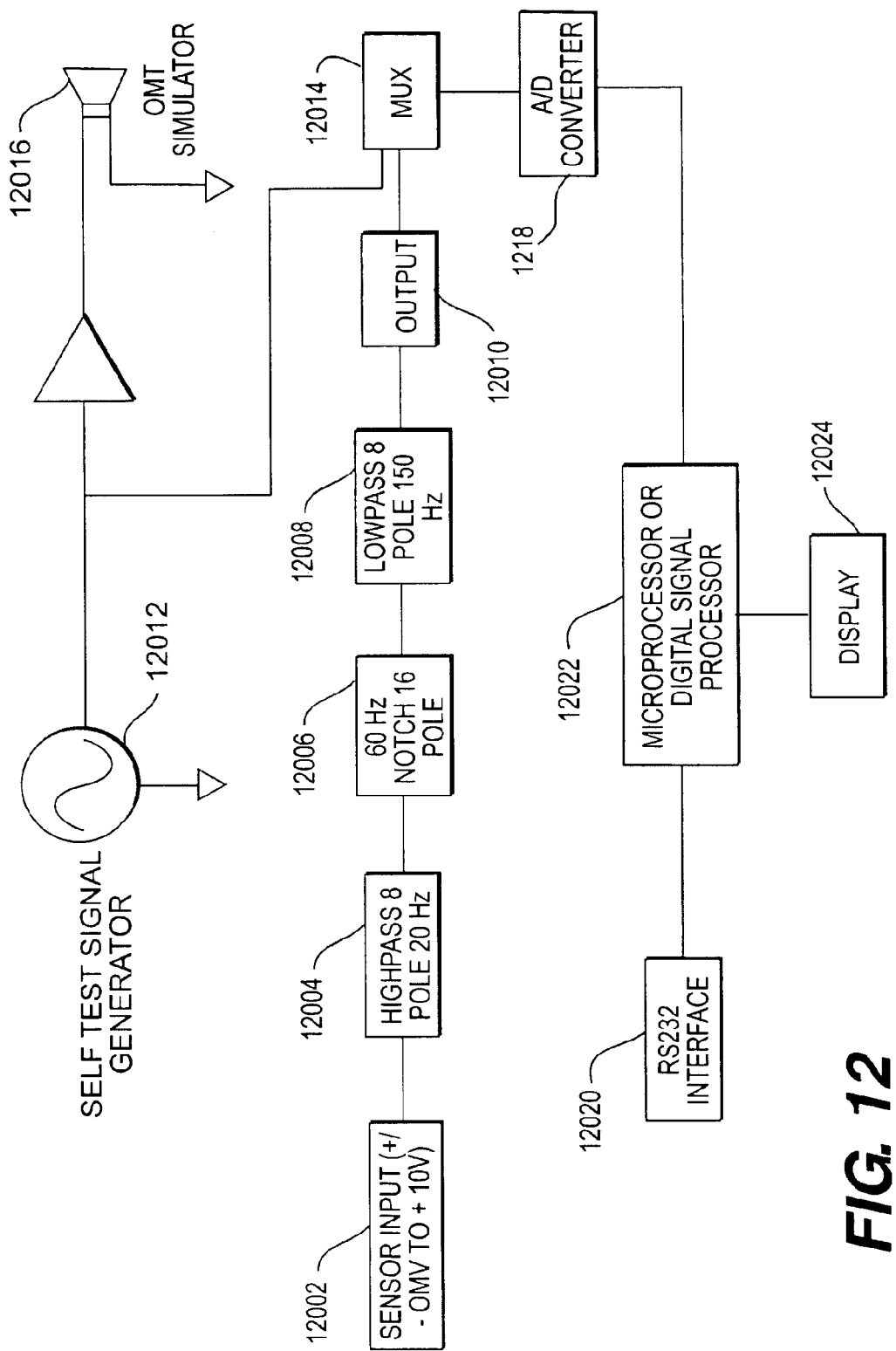
FIG. 12 is a block diagram of the system electronics for an eye tremor monitoring apparatus consistent with the present invention.
Figure 13:
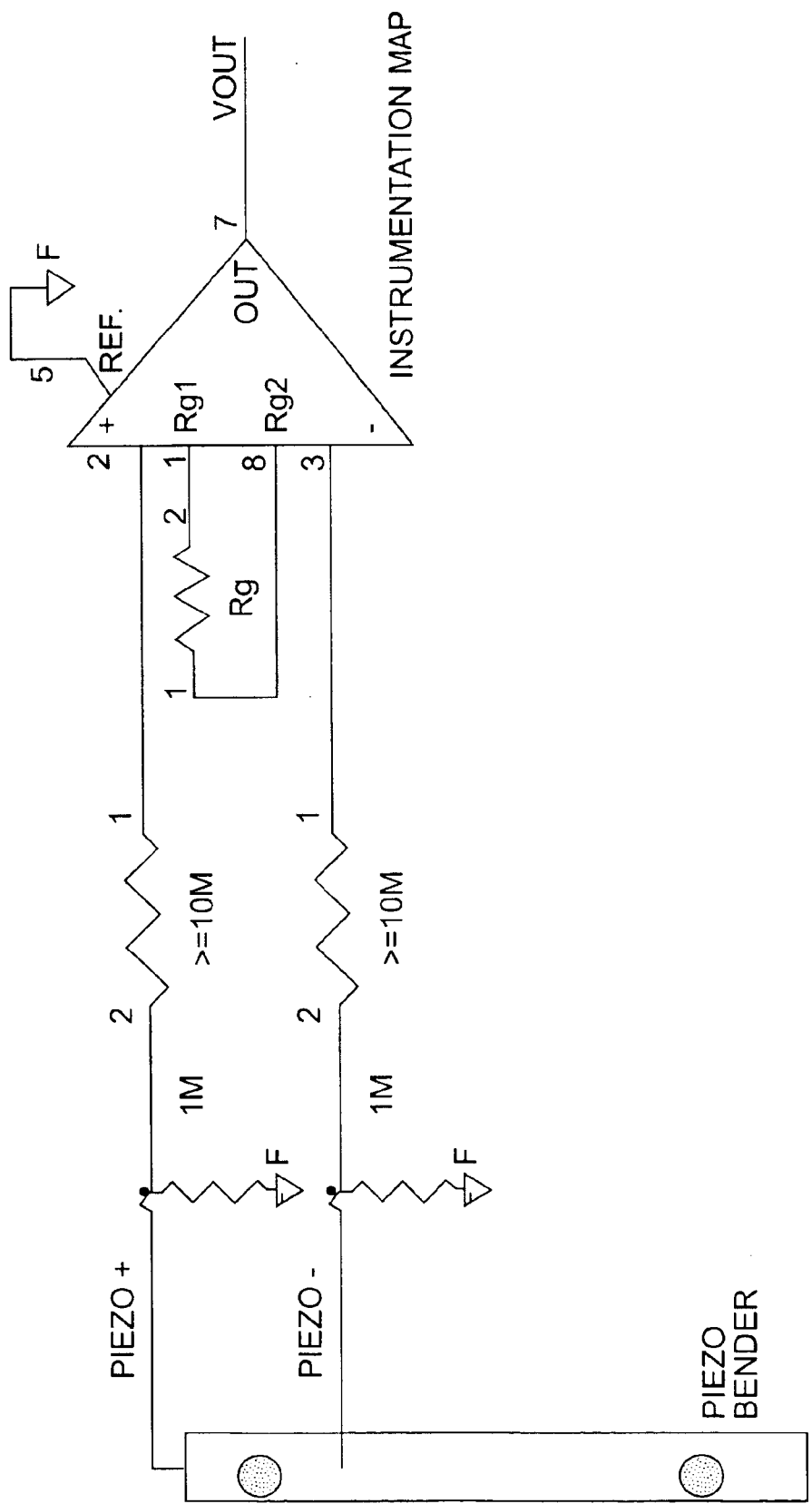
FIG. 13 is a schematic of a sensor instrumentation amplifier consistent with the present invention.

A block diagram of an embodiment of the sensor electronics consistent with the present invention is shown in FIG. 12. The system of FIG. 12 includes a sensor input module 12002, a high pass filter 12004, a notch filter 12006, a low pass filter 12008, an output module 12010, a self-test signal generator 12012, a multiplexer ("MUX") 12014, an OMT simulator 12016, an A/D converter 12108, an RS232 interface 12020, a microprocessor (or digital signal processor) 12022, and a display 12024. The sensor input module can also include, for example, a filter and amplifier circuit as shown in FIG. 13 placed near the piezoelectric bending element to improve sensor signal quality.

Figure 14:
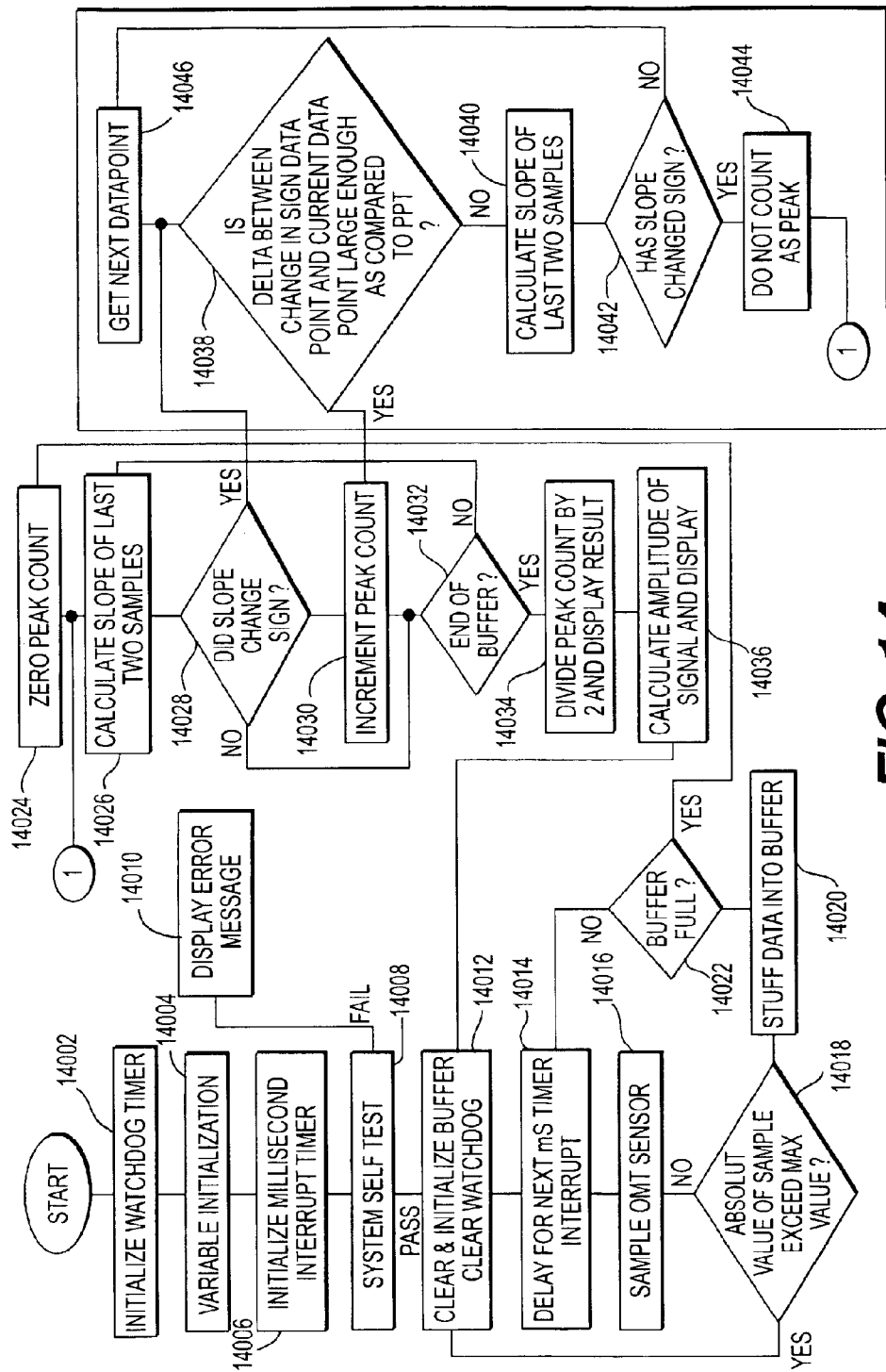
FIG. 14 is a flow diagram of a method for processing an eye tremor signal consistent with the present invention.

A flowchart of a method for processing an OMT signal consistent with an embodiment of the present invention, is shown in FIG. 14. Upon program startup, initialization steps 14002, 14004, and 14006 initialize a watchdog timer, variables, and an interrupt timer, respectively. After initialization, a self-test is performed on the system (step 14008). The self test capability allows an operator to verify the functionality of the system prior to use.

The self test procedure electronically disconnects the OMT sensor from the measurement electronics and switches in an oscillator of known frequency with an amplitude of approximately 300 mV full scale into the input. This allows the software to perform a self-test on the instrumentation electronics, independent of the sensor, prior to testing any input from a sensor. Once performance of the instrumentation electronics is verified, the functionality of the sensor is verified by providing an "OMT simulator" on the outside of the electronics enclosure. The OMT simulator may be, for example, a piezoelectric or electromagnetic actuator (audio speaker). To test the OMT sensor, the user places the sensor on the OMT simulator and selects "test sensor," for example, by depressing a button or by making a menu selection on the instrument's front panel. The instrument then performs the test by resonating the OMT simulator s actuator through a preset range of test frequencies, and checking the output to validate system performance over the range of frequencies required for the OMT measurement. The self-test mechanism can display the sensor state as "OK" or generate an error message such as "Bad Sensor" or "Low OMT Signal" (step 14010). An embodiment consistent with the present invention also can include the ability to adjust the signal strength, and provides an operator with a display indicating the signal level (e.g., an LED display showing the signal level spanning a scale from low to high).

Also, the message could serve as a prompt to the operator to test the system for proper functioning when absence of brain stem activity in the patient is possible. For example, in the event the patient being monitored is comatose and brain death is a possible reason for the "LOW OMT SIGNAL" message, the operator first verifies proper contact of the sensor with the subject's closed eyelid and remounts the sensor. If the system continues to display "LOW OMT SIGNAL," the operator activates the device S s self test mechanisms which test the instrumentation electronics both with and without the sensor as more fully described below. If the system is deemed to be working properly it could be concluded that the patient is brain dead.

After passing the system test, a buffer for collecting OMT signal data samples is initialized and cleared (step 14012). After a delay (if necessary) to synchronize with the next timer interrupt (step 14014), OMT sensor sampling begins (step 14016).

To measure OMT, an embodiment consistent with the present invention samples the sensor output voltage with an analog to digital converter at a rate of 500 Hz. The data is monitored and tested to see whether the amplitudes are within the required voltage range, for example, within the range of 0.1 to 4.0 volts (step 14018). If the amplitudes are larger than that of normal OMT, then this indicates that microsaccades likely occurred and that the data collected during the saccades should be given little if any weight. These data are ignored (for frequency analysis) and a message may be displayed indicating that an amplitude error has occurred. At which point process flow returns to step 14012 to clear the collected data from the buffer, reset the watchdog timer, and reinitiate OMT sensor sample collection (step 14016). Valid samples are loaded into the buffer (step 14020). Once the desired number of microsaccade free samples are obtained (step 14022), frequency and amplitude analysis on the data can be performed.

A number of techniques can be used for processing the OMT sensor data, including, by way of example: fast fourier transform (FFT) analysis, linear predictive modeling (LPM), and peak counting. Using the peak counting approach, the signal received by the sensor is sampled at a fixed interval (e.g., 1 millisecond) (step 14024). The first derivative (slope) of samples is computed (step 14026). A change in the sign of the slope with respect to the previous two data points indicates a peak (or valley) in the signal (step 14028). When a peak or valley is detected, a variable representing peak count is incremented (step 14030). After a selected number of samples have been processed (e.g., corresponding to a buffer size of 250 samples)(step 14032), the frequency is obtained by dividing the sum of the peaks and valleys by two (step 14034). This peak frequency is then displayed on the indicator. Multiple averaged peak readings can also be computed and displayed (step 14036). Computing an average reduces the noise in the OMT measurement.

There are multiple techniques for measuring the amplitude of the OMT signal. The peak-to-peak method uses the difference between the maximum and minimum signal value to determine the amplitude. The root mean square (RMS) method is another algorithm for computing the amplitude. As described in greater detail above, the amplitude change between successive samples of the signal is computed. To avoid counting natural resonance or ambient noise present in the environment, steps consistent with a "delta filter" can be executed to improve signal reception. If the amplitude change between samples is less than a preprogrammed threshold (PPT) (step 14038), the signal is monitored until the amplitude exceeds the PPT, and the Peak Count Algorithm (PCA) is updated (14030). If the signal changes direction before it exceeds the PPT (steps 14040 and 14042), the PCA is not updated (step 14044). If the slope has not changed sign, new signal datapoints are acquired (step 14046). The PPT is set based on measured ambient noise in the environment while the sensor is stable but free of contact.

Figure 15:
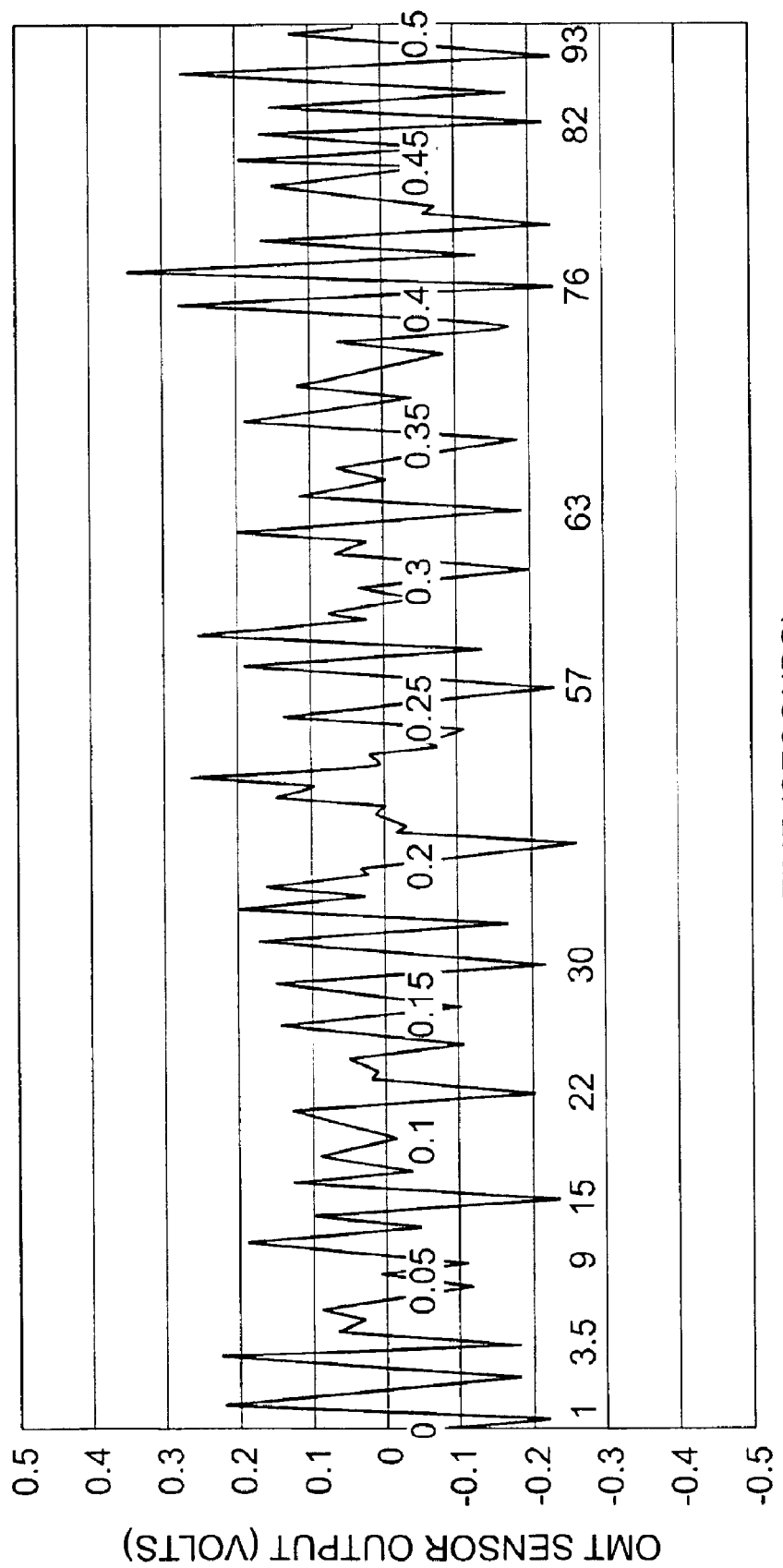
FIG. 15 is a plot of eye tremor signal consistent with the present invention.

FIG. 15 is a plot of a waveform indicative of OMT sensor output over time. The 0.5 second window shown in FIG. 15 includes ninety-three peaks, which results in a 93 Hz. OMT frequency. An embodiment consistent with the present invention provides a realtime display of the OMT signal so that an operator can have feedback, in addition to the measured frequency and amplitude, to gain insight into other significant monitoring information, including, for example, an indication of the quality of the OMT signal, the presence of a very low frequency or low amplitude OMT signal that may be encountered in comatose patients, and a "flat line" signal, which would indicate brain death, and which cannot generally be measured by frequency measurements alone.

Figure 16:
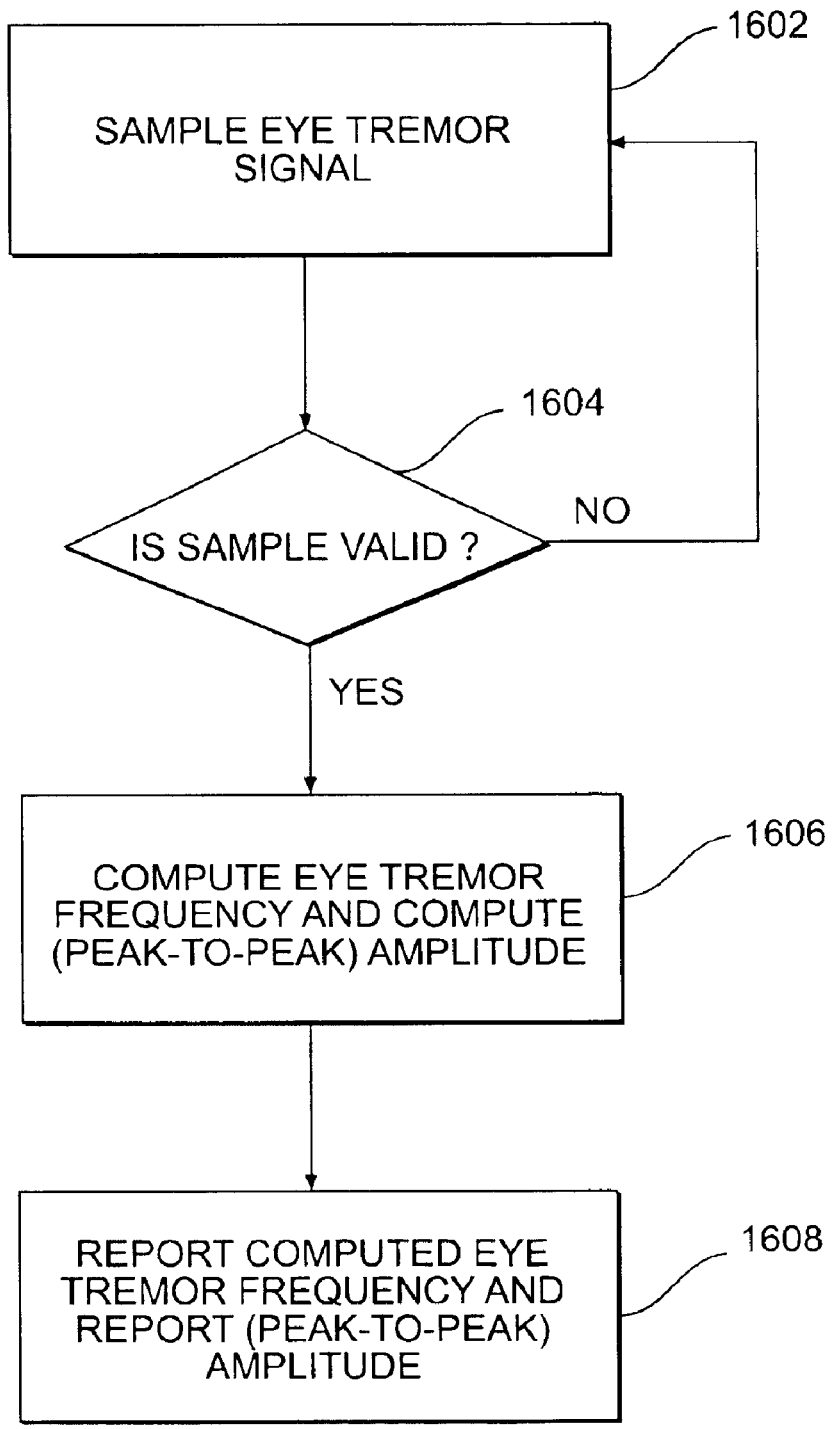
FIG. 16 is a flow diagram of a method for processing an eye tremor signal consistent with the present invention.

FIG. 16 is an embodiment of a method for monitoring a subject's eye tremor consistent with the present invention.

The processor samples the eye tremor signal received by the sensor (step 1602). The sampling can also take place after buffering the received signal, which is also real-time monitoring of the signal while receiving it. The eye tremor signal should be sampled at a rate that is at least twice the highest frequency in the received signal according to the Nyquist sampling theorem. For example, an eye tremor signal of 150 hz should be sampled at rate at least equal to 300 hz. Acquired samples can be tested to determine whether they are valid; for example, determining whether they are within an appropriate range to conform to physiological phenomenon (step 1604). One measure of validity, for example, is the amplitude of the sampled signal. An unusually large signal amplitude could be indicative of a microsaccade instead of an eye tremor and such microsaccade signals can be eliminated from the calculation of eye tremor frequency. Eye tremor frequency and amplitude are computed from valid samples (step 1606). Optionally, the computed eye tremor frequency and amplitude are reported or displayed (step 1608).

Figure 17:
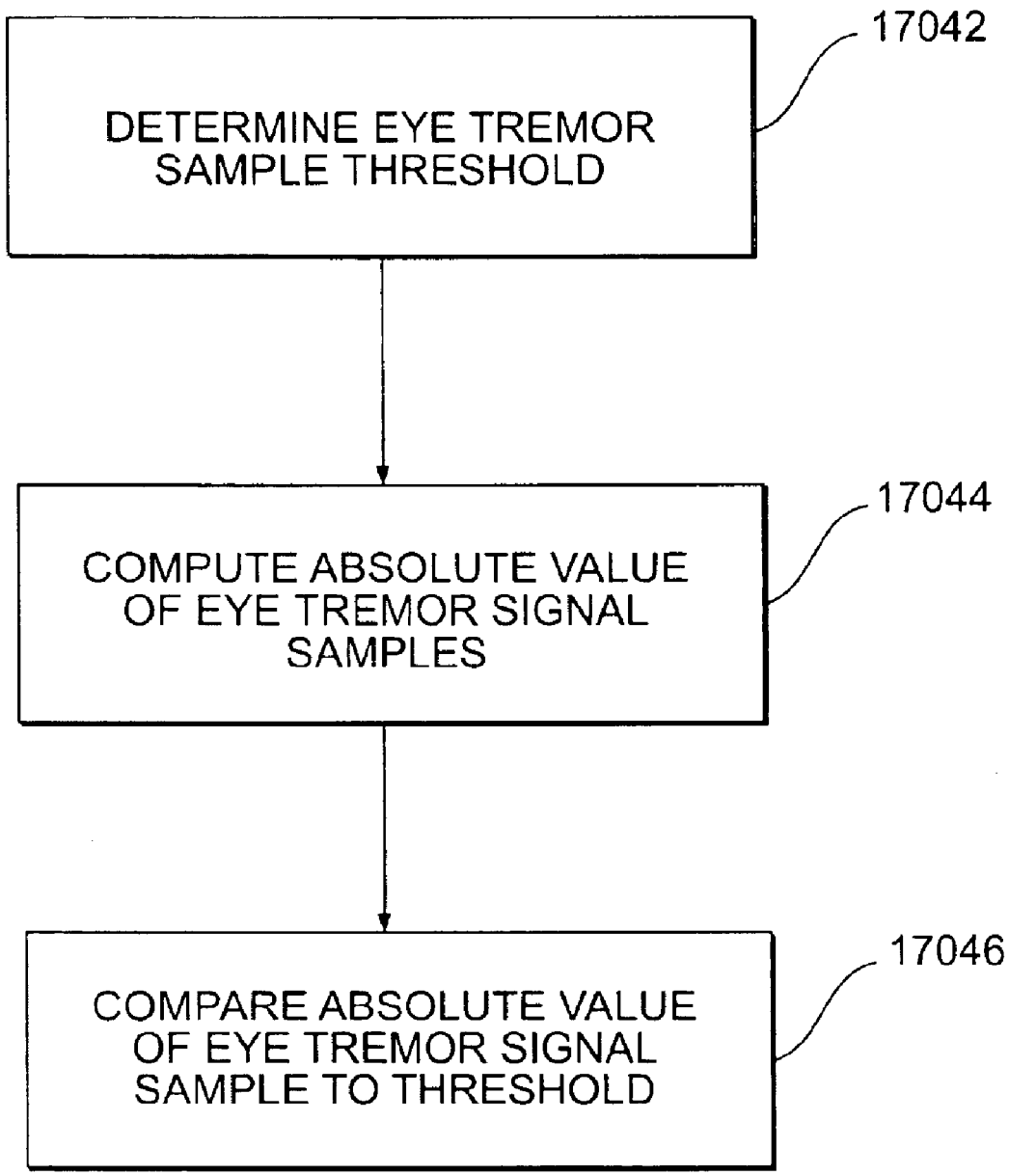
FIG. 17 is a flow diagram of a method for processing an eye tremor signal consistent with the present invention.

FIG. 17 is an embodiment of a method for determining whether a sampled eye tremor signal is valid (step 1604). An eye tremor threshold is determined to establish a boundary between valid and invalid eye tremor signal samples (step 17042). One skilled in the art will recognize that there are several suitable sources for this threshold. For example, the threshold can be set in advance or input by a user. The processor can also learn an appropriate threshold from the eye tremor signal automatically, using, for example, adaptive signal processing techniques. Consistent with an embodiment of this invention, an appropriate threshold is a value that distinguishes the signal amplitude of an eye tremor signal from a microsaccade. An example of a suitable threshold for this purpose is 4.0 volts.

The sampled signal can be processed to transform it to a form that is comparable to a threshold. One appropriate transformation is computing the absolute value of the eye tremor signal sample (step 17044). Other functions such as half wave and full wave rectification may be used to sample these data for their amplitude levels. These amplitude levels can provide the absolute value of eye tremor and may subsequently be checked for their validity (and elimination of gross eye movements and microsaccades from the frequency analyses). The processor then compares the transformed signal sample to the threshold. For example, the processor compares the absolute value of the eye tremor signal sample to the threshold (step 17046). Samples having an absolute value greater than the threshold can be declared invalid samples and are not used in the eye tremor frequency and amplitude computation.

Figure 18:
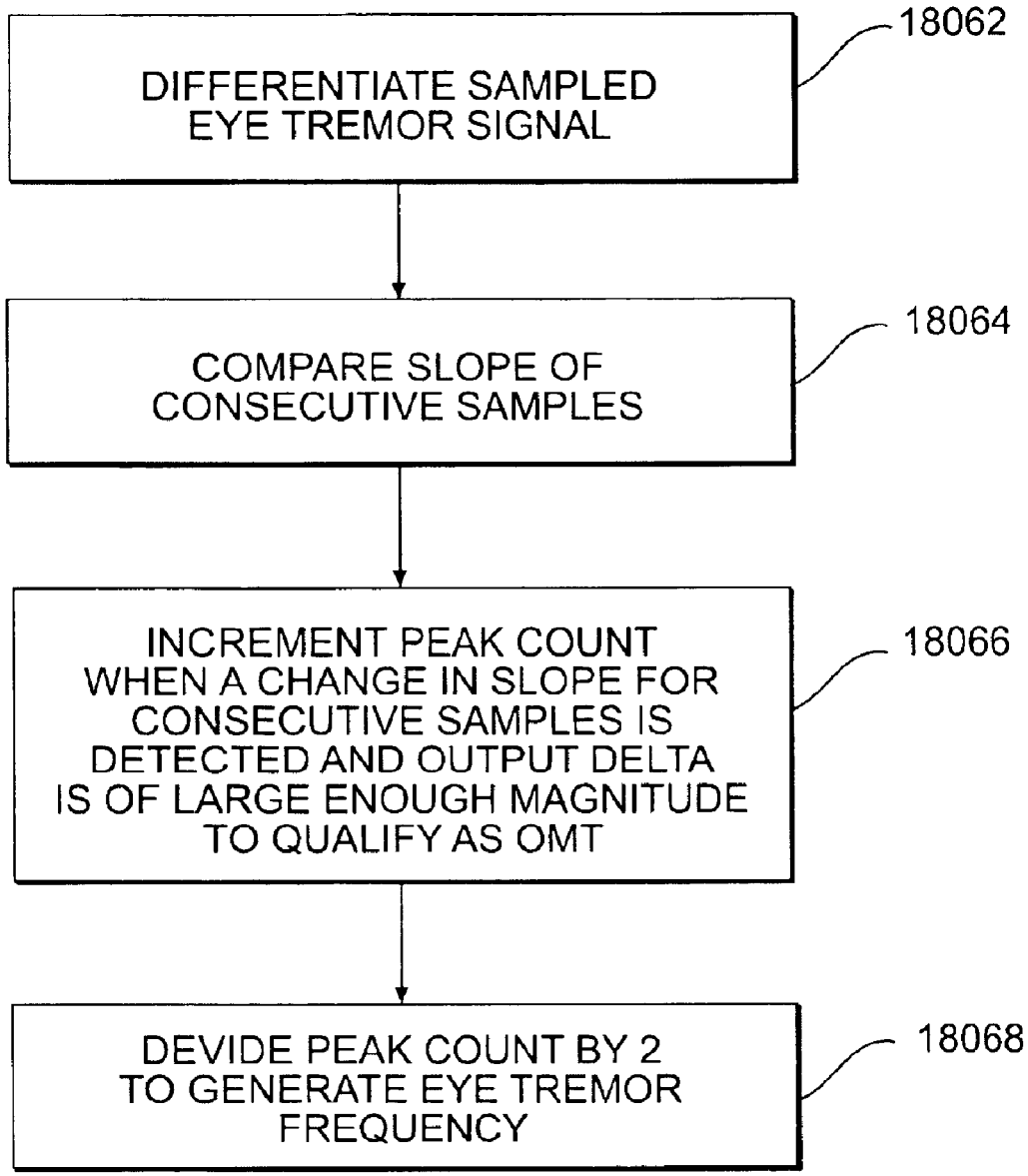
FIG. 18 is a flow diagram of a method for processing an eye tremor signal consistent with the present invention.

The processor computes eye tremor frequency and amplitude using valid sample signals (step 18062) as shown, for example, in FIG. 18. The processor differentiates the sampled, validated eye tremor signal (step 18062). The slopes of consecutive samples are compared (step 18064). A peak count is incremented when the processor detects a change in slope for consecutive samples and the change in output has a large enough magnitude to quality as OMT (step 18066). The resulting peak count is divided by two to generate a value for eye tremor frequency (step 18068).

Figure 19:
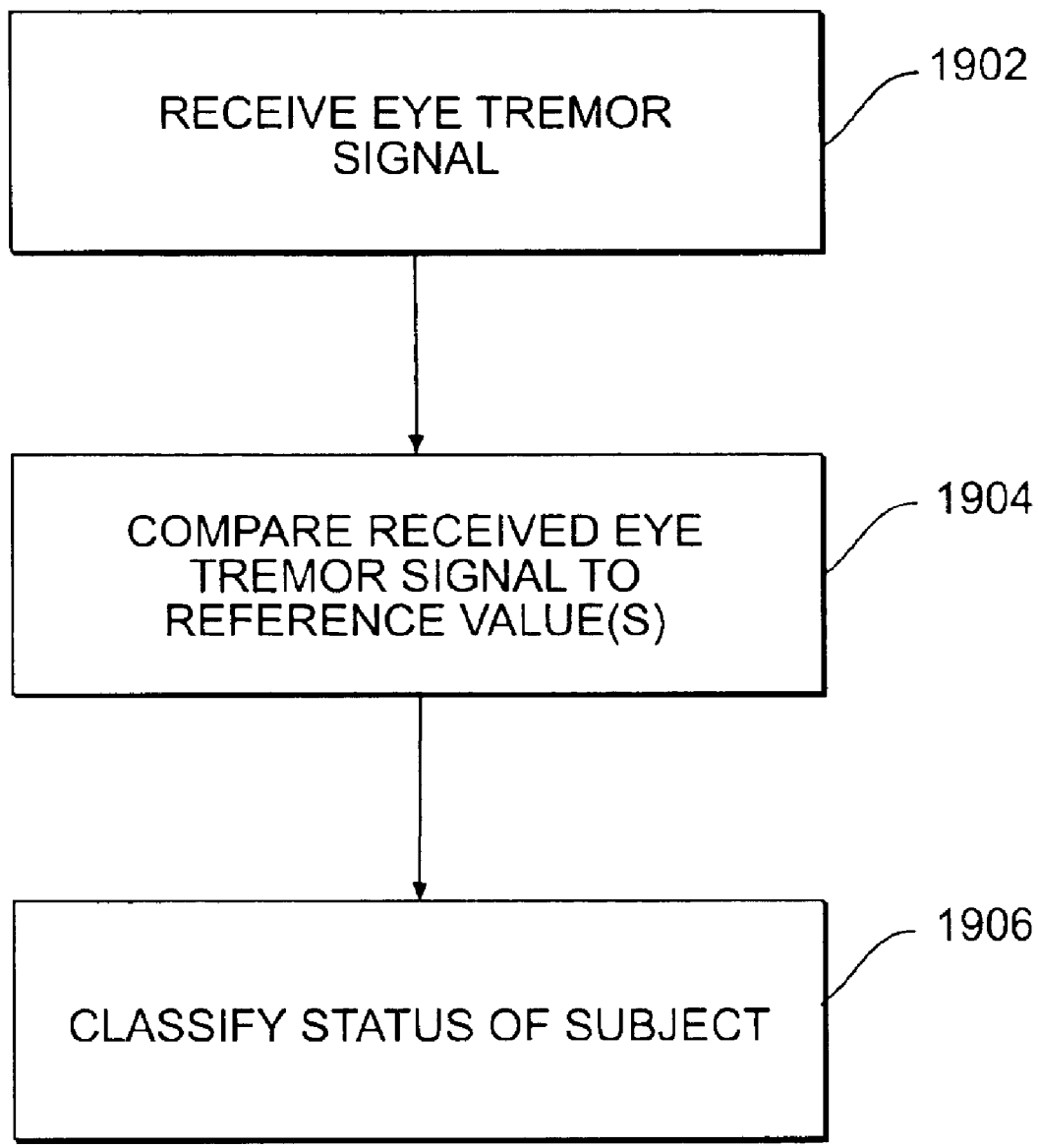
FIG. 19 is a flow diagram of a method for processing an eye tremor signal consistent with the present invention.

A flow diagram of a signal analysis classification method for detecting abnormal records in clinical situations, such as depth of anesthesia, prognosis of coma, diagnosis for brain stem death, multiple sclerosis, Parkinson's disease, presence of pharmacological agents or other conditions which cause or may cause a change in brainstem function is shown in FIG. 19. An OMT system consistent with the present invention receives an eye tremor signal (step 1902). The system compares the received eye tremor signal to at least one reference value (step 1904). The reference values correlate with different diagnostic classifications (see, for example, the patient studies cited supra). These reference values can be, for example, predetermined, computed, or selected from a range of candidate reference values. From the comparison at step 1904, the status of the subject being monitored is classified, e.g., the system reports the subject's depth of anesthesia (step 1906).

While some embodiments have been described, various changes and modifications may be made, and equivalents may be substituted. In addition, many modifications may be made to adapt a particular element, technique or implementation to the teachings of the present invention without departing from the central scope of the invention. For example, disclosed elements may be implemented in hardware, computer program code, or a combination of both hardware and computer program code. Moreover, elements depicted and described separately may be combined and implemented in a single element or distributed across a computer network. Therefore, this invention is not limited to the particular embodiments and methods disclosed, but includes all embodiments falling within the scope of the appended claims.

We claim:

1. A method for classifying a patient's brain stem function using eye tremor, comprising:

receiving a signal representing eye tremor;

comparing said received signal representing eye tremor to at least one reference value;

classifying the patient's brain stem function using said comparison of said received signal representing eye tremor to at least one reference value; and filtering microsaccades.

2. A method for classifying a patient's brain stem function using eye tremor, comprising:

receiving a signal representing eye tremor;

comparing said received signal representing eye tremor to at least one reference value;

classifying the patient's brain stem function using said comparison of said received signal representing eye tremor to at least one reference value; and selecting an eye tremor signal window.

3. A method for classifying a patient's brain stem function using eye tremor, comprising:

receiving a signal representing eye tremor;

comparing said received signal representing eye tremor to at least one reference value;

classifying the patient's brain stem function using said comparison of said received signal representing eye tremor to at least one reference value; and reducing signal interference from a power supply.

4. A method, executed by a processor, for classifying a patient's brain stem function using eye tremor, comprising:

receiving a signal representing eye tremor;

comparing said received signal representing eye tremor to at least one reference value;

classifying the patient's brain stem function using said comparison of said received signal representing eye tremor to at least one reference value; and filtering microsaccades.

5. A method, executed by a processor, for classifying a patient's brain stem function using eye tremor, comprising:

receiving a signal representing eye tremor;

comparing said received signal representing eye tremor to at least one reference value;

classifying the patient's brain stem function using said comparison of said received signal representing eye tremor to at least one reference value; and selecting an eye tremor signal window.

6. A method, executed by a processor, for classifying a patient's brain stem function using eye tremor, comprising:

receiving a signal representing eye tremor;

comparing said received signal representing eye tremor to at least one reference value;

classifying the patient's brain stem function using said comparison of said received signal representing eye tremor to at least one reference value; and reducing signal interference from a power supply.

* * * * *